(12) United States Patent
Collado-Cano et al.

(10) Patent No.: US 7,081,481 B2
(45) Date of Patent: Jul. 25, 2006

(54) EXCITATORY AMINO ACID RECEPTOR MODULATORS

(75) Inventors: Ivan Collado-Cano, Madrid (ES); Maria Rosario Gonzalez-Garcia, Madrid (ES); Beatriz López De Uralde-Garmendia, Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 316 days.

(21) Appl. No.: 10/276,532

(22) PCT Filed: May 24, 2001

(86) PCT No.: PCT/US01/10832

§ 371 (c)(1), (2), (4) Date: Jun. 20, 2003

(87) PCT Pub. No.: WO01/92213

PCT Pub. Date: Dec. 6, 2001

(65) Prior Publication Data

US 2004/0102521 A1    May 27, 2004

(30) Foreign Application Priority Data

May 31, 2000    (EP) ................... 00500109

(51) Int. Cl.
*A61K 31/197*    (2006.01)
*C07C 229/28*    (2006.01)

(52) U.S. Cl. .................. 514/561; 514/562; 560/115; 560/157; 560/222; 562/506

(58) Field of Classification Search ............... 560/115, 560/157, 222; 562/506; 514/561, 562
See application file for complete search history.

(56) References Cited

U.S. PATENT DOCUMENTS

| 6,172,058 B1 | 1/2001 | Tercero et al. |
| 6,498,180 B1 | 12/2002 | Collado et al. |
| 6,504,052 B1 | 1/2003 | Collado et al. |

FOREIGN PATENT DOCUMENTS

| EP | 0 870 760 A | 10/1998 |
| WO | WO 01/92212 A1 | 12/2001 |

OTHER PUBLICATIONS

Baskys et al., Understanding regulation of nerve cell death by mGluRs as a method for development of successful neuroprotective strategies, Journal of the Neurological Sciences 229-230 (2005) 201-209.*

FDA mulls drug to slow late-stage Alzheimer's [online], [retrieved on Sep. 23, 2003]. Retrieved from the internet, URL; http://www.cnn.com/2003/HEALTH/conditions/09/24/alzheimers.drug.ap/index.html>.*

Pellicciari et al: "Synthesis and Pharmacological Characterization of All Sixteen Stereoisomers of 2-(2'-Carboxy-3'-phenylcyclopropyl)glycine . Focus on (2S, 1'S,2'S,3'R)-2-(2'-Carboxy-3'-phenylcy clopropyl)glycine, a Novel and Selective Group II Metabotropic Glutamate Receptor Antagonist" Journal of Medicinal Chemistry, American Chemical Society. Washington, US, vol. 39, No. 11, 1996, pp. 2259-2269, XP002122695 ISSN: 0022-2623 cited in the application pp. 2259-2269.

Collado, Ivan et A., (2S,1'S,2' R,3'R)-2-(2'-Carboxy-3'-hydroxymethylcyclopropyl) Glycine Is a Highly Potent Group 2 and 3 Metabotropic Glutamate Receptor Agonist with Oral Activity, J. Med. Chem, 2004, 456-466, vol. 47.

Johnson, Byran G. et al, [²H]-LY341495 as a novel antagonist radioligand for group II metabotropic glutamate {mGlu} receptors: characterization of binding to membranes of mGlu receptors subtype expressing cells, Neuropharmacology, 1999, 1519-1529 vol. 38.

* cited by examiner

*Primary Examiner*—Kamal A. Saeed
*Assistant Examiner*—Rebecca Anderson
(74) *Attorney, Agent, or Firm*—Arvie J. Anderson; Mark A. Winter

(57) ABSTRACT

Compounds of the formula (I) in which: $R^1$ is $(CH_2)_n Y$; n is 1 or 2; Y is $NHSO_2 R^2$ or $X^1$—W—$X^2$—$R^3$; $X^1$ is O or NH; W is C=O, C=S, C=NH, or $SO_2$; $X^2$ is O or NH, provided that $X^1$ and $X^2$ are not both O; $R^2$ is $C_{1-10}$ alkyl; $C_{2-10}$ alkenyl; $C_{2-10}$ alkynyl; aryl; aryl-$C_{1-10}$ alkyl; aryl-$C_{2-10}$ alkenyl; aryl-$C_{2-10}$alkynyl; $C_{3-8}$ cycloalkyl or $C_{3-8}$-cycloalkyl-$C_{1-10}$ alkyl; and $R^3$ is hydrogen, $C_{1-10}$alkyl; $C_{2-10}$ alkenyl; $C_{2-10}$ alkynyl; aryl; aryl-$C_{1-10}$ alkyl; aryl-$C_{2-10}$ alkenyl; aryl-$C_{2-10}$ alkynyl; $C_{3-8}$ cycloalkyl; or $C_{3-8}$-cycloalkyl-$C_{1-10}$ alkyl; or a salt or ester thereof, modulate metabotropic glutamate receptor function and are useful in treating disorders of the central nervous system.

11 Claims, No Drawings

EXCITATORY AMINO ACID RECEPTOR MODULATORS

This application is a U.S. national phase entry, prudent to 35 USC 371, of PCT/US01/10832, filed May 24, 2001 and published on Dec. 6, 2001, International Publication No. WO01/92213, which claims the benefit of European Application No. 00500109.4.0 filed May 31, 2000.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D or C, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Compounds which modulate the function of these receptors, in particular agonists and antagonists of glutamate, are useful for the treatment of acute and chronic neurodegenerative conditions, and as antipsychotic, anticonvulsant, analgesic, anxiolytic, antidepressant, and antiemetic agents.

Pellicciari et al., *J. Med. Chem.*, 1996, 39, 2259–2269 refers to compounds known as metabotropic glutamate receptor agonists, in particular (2S,1'S,2'S)-2-(2-carboxycyclopropyl)glycine, also known as L-CCG-I; (2S,1'S,2'R,3'R)-2-(2'-carboxy-3'-(methoxymethyl)cyclopropylglycine, also known as cis-MCG-I; (2S,1'S,2'R,3'S)-2-(2'-carboxy-3'-(methoxymethyl)cyclopropylglycine, also known as trans-MCG-I; and (2S,1'R,2'R,3'R)-2-(2',3'-dicarboxy-cyclopropyl)glycine, also known as DCG-IV. The paper also describes the synthesis of the sixteen possible stereoisomers of 2-(2'-carboxy-3'-phenylcyclopropyl)glycine and their evaluation as excitatory amino acid receptor ligands. The compound (2S,1'S,2'S,3'R)-2-(2'-carboxy-3'-phenylcyclopropyl)glycine, also known as PCCG 4 is reported to be a metabotropic glutamate receptor antagonist.

Japanese patent application publication number JP 06179643 discloses MCG and generically discloses (2S,1'S,2'R)-2-(2-carboxy-3-alkoxymethyl- and 3-aralkoxymethyl-cyclopropyl)glycines as glutamate receptor agonists.

International patent application publication number WO 97/19049 discloses PCCG 4 and also generically discloses various 2-carboxy-3-arylcyclopropylglycines having affinity for metabotropic glutamate receptors.

International patent application publication number WO 98/00391 discloses 2-carboxy-3,3-dihalocyclopropylglycines, including (2S,1'S,2'S)-2-(2-carboxy-3,3-difluoro)cyclopropylglycine as metabotropic glutamate receptor agonists.

European patent application, publication number EP-A1-0870760 discloses that certain 3-substituted 2-carboxycyclopropyl glycine derivatives are modulators of metabotropic glutamate receptor function. The preferred compounds are said to be those in which the substituents at the 1 and 2 positions are in a trans relationship. The examples illustrate such compounds in which the substituents at the 1 and 3 positions are also in a trans relationship. One such compound is (2S,1'S,2'S,3'S)-2'-carboxy-3'-methylcyclopropylglycine.

Surprisingly, novel 3-substituted 2-carboxycyclopropyl glycine derivatives have now been found which are potent agonists of glutamate at metabotropic glutamate receptors.

Accordingly, the present invention provides a compound of the formula:

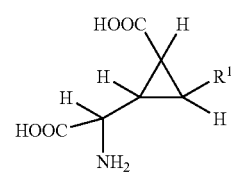

in which:

R$^1$ is (CH$_2$)$_n$Y;

n is 1 or 2;

Y is NHSO$_2$R$^2$ or X$^1$—W—X$^2$—R$^3$;

X$^1$ is O or NH;

W is C=O, C=S, C=NH, or SO$_2$;

X$^2$ is O or NH, provided that X$^1$ and X$^2$ are not both O;

R$^2$ is C$_{1-10}$ alkyl; C$_{2-10}$ alkenyl; C$_{2-10}$ alkynyl; aryl; aryl-C$_{1-10}$ alkyl; aryl-C$_{2-10}$ alkenyl; aryl-C$_{2-10}$ alkynyl; C$_{3-8}$ cycloalkyl or C$_{3-8}$-cycloalkyl-C$_{1-10}$ alkyl; and R³ is hydrogen, $C_{1-10}$ alkyl; $C_{2-10}$ alkenyl; $C_{2-10}$ alkynyl; aryl; aryl-$C_{1-10}$ alkyl; aryl-$C_{2-10}$ alkenyl; aryl-$C_{2-10}$ alkynyl; $C_{3-8}$ cycloalkyl; or $C_{3-8}$-cycloalkyl-$C_{1-10}$ alkyl;

or a salt or ester thereof.

Compounds of the invention have been found to be agonists of glutamate at metabotropic glutamate receptors and are therefore useful in the treatment of diseases of the central nervous system such as neurological diseases, for example neurodegenerative diseases, and as antipsychotic, anxiolytic, drug-withdrawal, antidepressant, anticonvulsant, analgesic and anti-emetic agents.

It will be appreciated that the compounds of formula (I) contain at least four asymmetric carbon atoms, three being in the cyclopropane ring and one being at the α-carbon of the amino acid group. Accordingly, the compounds of the invention may exist in and be isolated in enantiomerically pure form, in racemic form, or in a diastereoisomeric mixture.

Preferred compounds of the invention are those of the formula

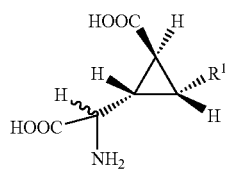

Ia

The amino acid moiety preferably has the natural amino configuration. Accordingly, preferred compounds according to the invention are those of the formula:

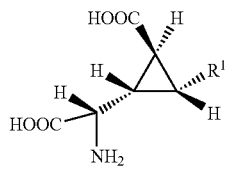

Ib

The terms alkyl, alkenyl and alkynyl refer to straight chain or branched groups.

A $C_{1-10}$ alkyl group includes a $C_{1-4}$ alkyl group and can be straight or branched chain, such as, for example, methyl, ethyl, propyl, isopropyl, butyl and isobutyl, and is preferably methyl or ethyl. The term $C_{1-10}$ alkyl also includes $C_{1-8}$ alkyl and $C_{1-6}$ alkyl. Other particular values are t-butyl, pentyl, hexyl, heptyl, octyl, nonyl and decyl.

A $C_{2-10}$ alkenyl group includes, for example, vinyl, prop-2-enyl, but-3-enyl, pent-4-enyl and isopropenyl, and an alkenyl group can contain more than one double bond and, in addition, one or more triple bonds. An example of an alkenyl group containing more than one double bond is an alkadienyl group, such as 1,3-butadienyl. A preferred alkenyl group is of the formula R'—CH=CH—(CH₂)ᵣ— where R' is hydrogen or $C_{1-4}$ alkyl and r is 0, 1 or 2. The term $C_{2-10}$ alkenyl also includes $C_{3-10}$ alkenyl.

The term $C_{2-10}$ alkynyl includes $C_{3-10}$ alkynyl. A particular value is prop-2-ynyl. The term also includes groups containing more than one triple bond.

The term aryl group, as such or in an aryl-$C_{1-10}$ alkyl, aryl-$C_{2-10}$ alkenyl or aryl-$C_{2-10}$ alkynyl group, refers to an aromatic monocyclic or polycyclic carbocyclic ring that may be unsubstituted or substituted by one or more substituents, said substituents being selected from atoms and groups that, when present in the compound of formula I, do not prevent the compound of formula I from functioning as a metabotropic glutamate receptor agonist.

Examples of an aromatic monocyclic or polycyclic carbocyclic ring in an aryl group include phenyl and naphthyl.

An aromatic monocyclic or polycyclic carbocyclic ring in an aryl group may be unsubstituted or substituted with, for example, one, two or three substituents selected independently from halogen, cyano, nitro, amino, (1–4C)alkylamino, di(1–4C)alkylamino, carboxy, and a group of formula —$(CH_2)_m$—X—$(CH_2)_n$—$R^a$ in which m is 0, 1 or 2, n is 0, 1 or 2, $X^a$ represents a bond, O, S, SO, $SO_2$, NH, CO, COO, OCO, CONH, NHCO, NHCONH, $NHSO_2$ or $SO_2NH$ and $R^a$ represents an $C_{1-4}$ alkyl, $C_{2-4}$ alkenyl, $C_{2-4}$ alkynyl, halo $C_{1-4}$ alkyl or phenyl group which is unsubstituted or substituted by one or two substituents selected independently from halogen, (1–4C)alkyl and (1–4C)alkoxy.

An aryl group, as such or in an aryl-$C_{1-4}$ alkyl may be, for example, a phenyl group which is unsubstituted or substituted, for example with one or two substituents selected independently from halogen, $C_{1-4}$ alkyl and $C_{1-4}$ alkoxy. An example of an aryl group is phenyl. An example of an aryl-$C_{1-4}$ alkyl group is benzyl.

Examples of particular values for an aryl group include phenyl, 2-methoxyphenyl, 3-methoxyphenyl, 4-methoxyphenyl, 2-methylphenyl, 2,6-dimethylphenyl, 3-nitrophenyl, 3-acetylphenyl and 4-trifluoromethylphenyl.

The term $C_{3-8}$ cycloalkyl, as such or in the term $C_{3-8}$ cycloalkyl-$C_{1-10}$ alkyl, includes monocyclic and polycyclic groups. It includes $C_{3-6}$ cycloalkyl. Examples of particular values are cyclopropyl, cyclobutyl, cyclopentyl, cyclohexyl and bicyclo[2.2.2]octane.

Examples of particular values for $X^1$—W—$X^2$— are OCONH—, NHCONH— and NH(C=NH)NH.

It will be appreciated that compounds where $X^1$ and $X^2$ are both O would be expected to be chemically unstable; hence these compounds have been excluded by proviso from the definition of compounds according to the invention.

Examples of particular values for $R^2$ are:
for a $C_{1-10}$ alkyl or $C_{1-4}$ alkyl group: methyl or ethyl;
for an aryl group: phenyl; and
for an aryl-$C_{1-10}$ alkyl or aryl-$C_{1-4}$ alkyl group: benzyl.

Examples of particular values for $R^3$ are:
for a $C_{1-10}$ alkyl or $C_{1-4}$ alkyl group: methyl;
for an aryl group: phenyl, 2-methoxyphenyl, 3-methoxyphenyl, 4-methoxyphenyl, 2-methylphenyl, 2,6-dimethylphenyl, 3-nitrophenyl, 3-acetylphenyl and 4-trifluoromethylphenyl; and
for an aryl-$C_{1-10}$ alkyl or aryl-$C_{1-4}$ alkyl group: benzyl.

Examples of particular values for $R^1$ are:
phenylcarbamoyloxymethyl, 2-methoxyphenylcarbamoyloxymethyl, benzylcarbamoyloxymethyl, 3-methoxyphenylcarbamoyloxymethyl, 4-methoxyphenylcarbamoyloxymethyl, 2-methylphenylcarbamoyloxymethyl, 2,6-dimethylphenylcarbamoyl-oxymethyl, 3-nitrophenylcarbamoyloxymethyl, 3-acetylphenylcarbamoyloxymethyl, 4-trifluoromethylphenylcarbamoyloxymethyl, ethylcarbamoyloxymethyl, cyclohexylcarbamoyloxymethyl, (1-naphthyl)carbamoyloxymethyl, (3-methoxy)phenylcarbamoyloxymethyl, phenylureidomethyl, ethylureidomethyl, benzylureidomethyl, benzenesulfonylaminomethyl, phenylthioureidomethyl, phenylcarbamoyloxyethyl and phenylureidoethyl.

Another preferred group of compounds is that of formula

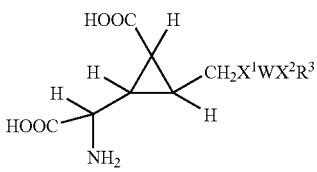

and pharmaceutically acceptable salts and esters thereof.

Particularly preferred compounds are:

(2SR,1'SR,2'RS,3'RS)-2-(3'-phenylcarbamoyloxymethyl-2'-carboxycyclopropyl)glycine;
(2SR,1'SR,2'RS,3'RS)-2-(3'-(2-methoxy)phenylcarbamoyloxymethyl-2'-carboxycyclopropyl)glycine;
(2SR,1'SR,2'RS,3'RS)-2-(3'-(3-methoxy)phenylcarbamoyloxymethyl-2'-carboxycyclopropyl)glycine;
(2SR,1'SR,2'RS,3'RS)-2-(3'-(4-methoxy)phenylcarbamoyloxymethyl-2'-carboxycyclopropyl)glycine;
(2SR,1'SR,2'RS,3'RS)-2-(3'-(2-methyl)phenylcarbamoyloxymethyl-2'-carboxycyclopropyl)glycine;
(2SR,1'SR,2'RS,3'RS)-2-(3'-(2,6-dimethyl)phenylcarbamoyloxymethyl-2'-carboxycyclopropyl)glycine;
(2SR,1'SR,2'RS,3'RS)-2-(3'-(3-nitro)phenylcarbamoyloxyymethyl-2'-carboxycyclopropyl)glycine;
(2SR,1'SR,2'RS,3'RS)-2-(3'-(3-acetyl)phenylcarbamoyloxymethyl-2'-carboxycyclopropyl)glycine;
(2SR,1'SR,2'RS,3'RS)-2-(3'-(4-trifluoromethyl)phenylcarbamoyloxymethyl-2'-carboxycyclopropyl)glycine;
(2SR,1'SR,2'RS,3'RS)-2-(3'-benzylcarbamoyloxymethyl-2'-carboxycyclopropyl)glycine;
(2SR,1'SR,2'RS,3'RS)-2-(3'-ethylcarbamoyloxymethyl-2'-carboxycyclopropyl)glycine;
(2SR,1'SR,2'RS,3'RS)-2-(3'-cyclohexylcarbamoyloxymethyl2'-carboxycyclopropyl)glycine;
(2SR,1'SR,2'RS,3'RS)-2-[3'-(1-naphthyl)carbamoyloxymethyl-2'-carboxycyclopropyl]glycine;
(2SR,1'SR,2'RS,3'RS)-2-[3'-(3-methoxy)phenylcarbamoyloxymethyl-2'-carboxycyclopropyl]glycine;
(2SR,1'SR,2'SR,3'RS)-2-(3'-phenylureidomethyl-2'-carboxycyclopropyl)glycine;
(2SR,1'SR,2'SR,3'RS)-2-(3'-benzylureidomethyl-2'-carboxycyclopropyl)glycine;
(2SR,1'SR,2'SR,3'RS)-2-(3'-ethylureidomethyl-2'-carboxycyclopropyl)glycine;
(2SR,1'SR,2'SR,3'RS)-2-(3'-benzenesulfonylaminomethyl-2'-carboxycyclopropyl)glycine;
(2SR,1'SR,2'SR,3'RS)-2-(3'-phenylthioureidomethyl-2'-carboxycyclopropyl)glycine;
(2SR,1'SR,2'SR,3'RS)-2-[(3'-(2''-phenylcarbamoyloxyethyl)-2'-carboxy)cyclopropyl]glycine;
(2SR,1'SR,2'SR,3'RS)-2-[(3'-(2''-phenylureidoethyl)-2'-carboxy)cyclopropyl]glycine;

and pharmaceutically acceptable salts and esters thereof.

The present invention includes salts of the formula (I) compounds. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula (I). The alkali metal and alkaline earth metal salts are generally prepared by the reaction of the hydroxide form of the desired metal salt with a compound of formula (I).

The salts of the compounds of formula I may be pharmaceutically-acceptable salts. However, other salts are included in the invention. They may serve as intermediates in the purification of compounds or in the preparation of other, for example pharmaceutically-acceptable, acid addition salts, or are useful for identification, characterisation or purification.

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, or organic sulphonic, 2-hydroxyethane sulphonic, toluene-p-sulphonic, or naphthalene-2-sulphonic acid.

The present invention includes esters of the formula (I) compounds, such esters being for example aliphatic esters such as alkyl esters.

The esters of the compounds of formula I may be pharmaceutically acceptable metabolically labile esters of compounds of formula I. These are ester derivatives of compounds of formula I that are hydrolyzed in vivo to afford said compound of formula I and a pharmaceutically acceptable alcohol. Examples of metabolically labile esters include esters formed with (1–6C) alkanols in which the alkanol moiety may be optionally substituted by a (1–8C) alkoxy group, for example methanol, ethanol, propanol and methoxyethanol. The most preferred esters are alkyl esters derived from $C_{1-4}$ alkanols, especially methyl and ethyl esters.

The invention also comprises a process for preparing a compound according to formula (I), or a salt or ester thereof, which comprises:

(a) deprotecting a compound of formula

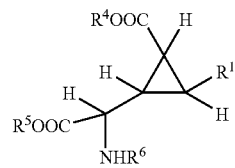

in which $R^4$ and $R^5$ each independently represents hydrogen or a carboxyl protecting group, and $R^6$ represents hydrogen or an amine protecting group;

(b) hydrolysing a compound of formula

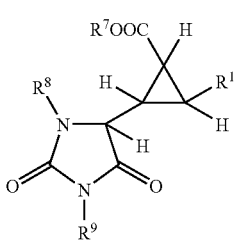

in which $R^7$ represents a hydrogen atom or a carboxyl protecting group, and $R^8$ and $R^9$ each independently represents a hydrogen atom, a $C_{1-4}$ alkyl group, a (2–6C)alkanoyl group, a $C_{3-4}$ alkenyl group or a phenyl $C_{1-4}$ alkyl group in which the phenyl group is unsubstituted or substituted by halo, $C_{1-4}$ alkyl, $C_{1-4}$ alkoxy; or (c) hydrolysing a compound of formula

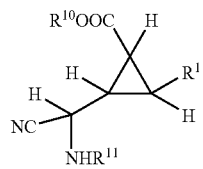

in which $R^{10}$ represents a hydrogen atom or a carboxy protecting group, and $R^{11}$ represents a hydrogen atom or an amine protecting group;

followed when necessary by recovering a diastereomer or isomer of the compound of formula I, or forming a salt or ester thereof.

The protection of carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl ($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and tbutyldimethylsilyl; and allyl groups such as allyl and 1-(trimethylsilylmethyl)prop-1-en-3-yl.

Examples of amine protecting groups include acyl groups, such as groups of formula $R^2$ CO in which $R^{12}$ represents $C_{1-6}$ alkyl, $C_{3-10}$ cycloalkyl, phenyl $C_{1-6}$ alkyl, phenyl, $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy. Preferred amino protecting groups include t-butoxycarbonyl (Boc) and benzyl.

Examples of particular values for $R^4$, $R^5$, $R^7$ and $R^{10}$ are hydrogen, methyl, ethyl, n-propyl, n-butyl, t-butyl, benzyl, 4-methoxybenzyl, phenylethyl and phenylpropyl.

Examples of particular values for $R^6$ and $R^{11}$ include acetyl and tert-butoxycarbonyl.

Examples of particular values for $R^8$ and $R^9$ are hydrogen and benzyl.

The compounds of formula (II) may be deprotected by conventional methods. Thus, an alkyl carboxyl protecting group may be removed by hydrolysis. The hydrolysis may conveniently be performed by heating the compound of formula (II) in the presence of either a base, for example an alkali metal hydroxide such as lithium, sodium or potassium hydroxide, or an alkaline metal hydroxide, such as barium hydroxide or an acid such as hydrochloric acid. The hydrolysis is conveniently performed at a temperature in the range of from 20° C. to 300° C. An aralkyl carboxyl protecting group may conveniently be removed by hydrogenation. The hydrogenation may be effected by reacting the compound of formula (II) with hydrogen in the presence of a Group VIII metal catalyst, for example a palladium catalyst such as palladium on charcoal. Suitable solvents for the reaction include alcohols such as ethanol. The reaction is conveniently performed at a temperature in the range of from 0° C. to 100° C.

An acyl, amine protecting group is also conveniently removed by hydrolysis, for example as described for the removal of an alkyl carboxyl protecting group. Thus, a tert-butoxycarbonyl, amine protecting group may conveniently be removed in the presence of an acid, for example hydrochloric acid or trifluoroacetic acid. The hydrolysis is performed in the presence of a solvent such as water, ethyl acetate or dichloromethane and at a temperature in the range of from 20° C. to 100° C.

The compounds of formula III are conveniently hydrolyzed in the presence of a base, for example an alkali metal hydroxide such as lithium, sodium or potassium hydroxide, or an alkaline earth metal hydroxide such as barium hydroxide. Suitable reaction media include water. The temperature is conveniently in the range of from 50° C. to 150° C.

The compounds of formula IV are conveniently hydrolyzed in the presence of an acid, such as hydrochloric acid or sulfuric acid, or a base, such as an alkali metal hydroxide, for example sodium hydroxide. The hydrolysis is conveniently performed in an aqueous solvent such as water, or in an alkanol such as methanol or ethanol, and at a temperature in the range of from 20° C. to 200° C.

Compounds of formula I in the form of diastereomeric mixtures or isomers may be obtained in a conventional manner, for example by chiral synthesis using chiral starting materials, of by using conventional separation techniques, for example by forming a crystalline salt with a chiral acid or base.

Compounds of formula (II) in which $R^5$ represents hydrogen may be prepared by a procedure analogous to that described in Ohfune Y., et al., J. Med. Chem., 1996, 39, 407–423. Thus they may be prepared by reacting a compound of formula

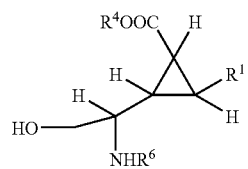

with an oxidising agent. Convenient oxidising agents include Jones Reagent.

Compounds of formula (V) may be prepared by reacting a compound of formula

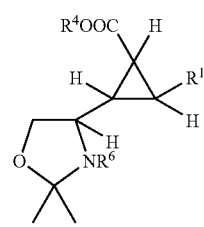

with a sulfonic acid, such as camphorsulfonic acid (CSA) and an alkanol, such as methanol.

Compounds of formula (VI) may be prepared by epimerizing an isomeric compound of formula

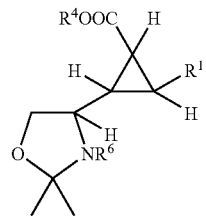

VII with a strong base, such as potassium hexamethyldisilane.

Compounds of formula (VII) may be prepared by reacting a compound of formula

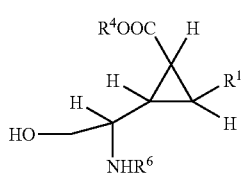

VIII with acetone dimethyl ketal in the presence of a sulfonic acid, such as camphorsulfonic acid.

Compounds of formula VIII may be prepared by selectively deprotecting a compound of formula

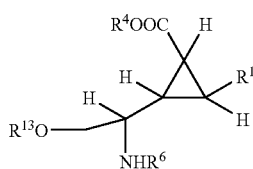

IX in which $R^{13}$ represents a hydroxyl protecting group, such as a tert-butyldimethylsilyl (TBS) group. A convenient reagent for removing a TBS group is camphorsulfonic acid in methanol.

The compounds of formula (IX) may be prepared by reacting a compound of formula

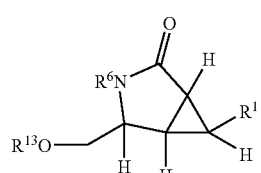

X with a base, such as lithium hydroxide, for example in tetrahydrofuran, followed by introduction of the protecting group $R^5$, for example by treatment with diazomethane (to afford a compound in which $R^5$ is methyl).

Compounds of formula (X) may be prepared by treating a compound of formula

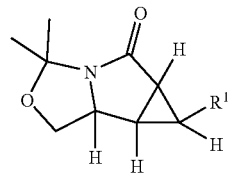

XI with an ion exchange resin, such as DOWEX 50W×8, followed by introduction of the protecting groups $R^6$ and $R^{13}$, for example by stepwise reaction with tributylsilyl chloride in the presence of imidazole, followed by Boc$_2$O in the presence of triethylamine and 4-dimethylaminopyridine.

Compounds of formula (XI) may be prepared by reacting a compound of formula

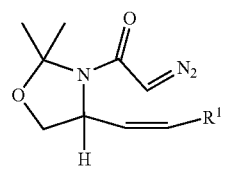

XII with palladium (II) acetate.

Compounds of formula (XII) may be prepared by diazotizing a compound of formula

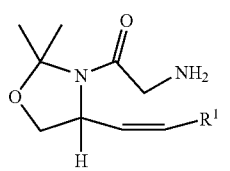

XIII for example by reaction with sodium nitrite.

Compounds of formula (XIII) may be prepared by selectively deprotecting a compound of formula

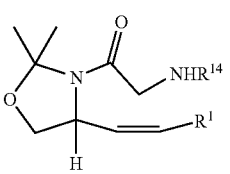

XIV in which $R^{14}$ represents an amine protecting group, such as t-butoxycarbonyl. For example a t-butoxycarbonyl (Boc) group may conveniently be removed by treatment with trimethylsilyl trifluoromethanesulfonate (TMSOTf) and 2,6-lutidine.

The compounds of formula (XIV) may be prepared by reacting a compound of formula

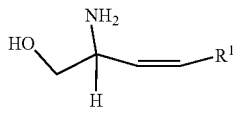

XV with an N-protected glycinate, such as N-hydroxysuccinimide N-(tert-butoxycarbonyl)glycinate, followed by reaction with acetone dimethylketal in the presence of a sulfonic acid such as p-toluenesulfonic acid.

The compounds of formula (XV) may be prepared by reacting a compound of formula

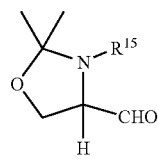

XVI in which $R^{15}$ represents an amine protecting group, such as t-butoxycarbonyl, with a triphenylphosphine halide of formula $Ph_3P^+CH_2R^1$ $A^-$, in which $A^-$ represents a halide ion such as bromide, in the presence of a strong base, such as potassium hexamethyldisilane, followed by removal of the amine protecting group, and hydrolysis of the acetonide, for example by reaction with methanolic HCl.

Compounds of formula (II) in which $R^1$ represents $(CH_2)_nY$ in which n is 1 or 2 may alternatively be prepared by reacting a compound of formula

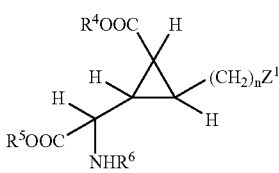

XVII in which n is 1 or 2 and $Z^1$ represents a leaving atom or group, such as a chlorine atom or a p-toluenesulfonyl group, with a salt of formula MY in which M represents an alkali metal such as sodium or potassium.

The compounds of formula (XVII) may be prepared by reacting a compound of formula

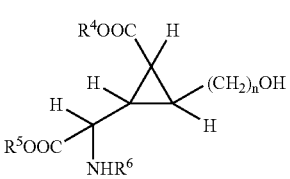

XVIII with a halogenating or sulphonating reagent such as ptoluenesulfonyl chloride.

The compounds of formula XVIII may be prepared either by hydrolysing a compound of formula XIX

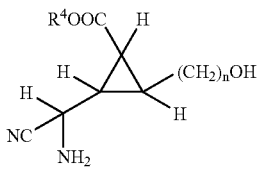

XIX for example using HCl in aqueous ethanol, followed by protecting the amino group, for example by reaction with $Boc_2O$ in tetrahydrofuran or dioxane in the presence of $NaHCO_3$, or by hydrolysing a compound of formula XX

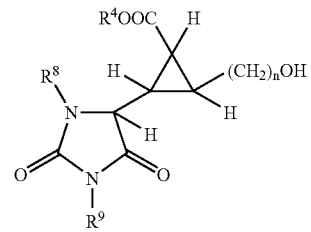

XX in the presence of a base, for example sodium hydroxide, in an aqueous solution at an elevated temperature, for example about 100° C., followed by protecting the carboxylic acid groups, for example using HCl in anhydrous ethanol, and protecting the amino group, for example by reaction with $Boc_2O$ in tetrahydrofuran or dioxane in the presence of $NaHCO_3$.

The compounds of formula XIX may be prepared by reacting a compound of formula XXI

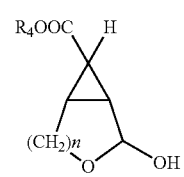

XXI with ammonium chloride and potassium cyanide in the presence of aluminium oxide. A convenient solvent is acetonitrile.

The compounds of formula XX may be prepared by hydrolysing a compound of formula XXI with an alkali metal hydroxide, for example using sodium hydroxide in aqueous ethanol, followed by treatment with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C.

Compounds of formula XXI may be prepared by oxidising a compound of formula XXII

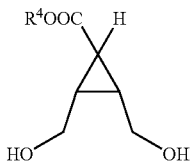

XXII for example by employing a Swern oxidation.

Compounds of formula XXII may be prepared by reacting a compound of formula

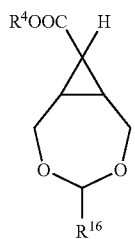

XXIII in which $R^{16}$ represents a hydrogen atom, a $C_{1-4}$ alkyl group or a phenyl group, with HCl or camphorsulphonic acid in an alkanol such as ethanol.

Compounds of formula XXIII may be prepared by reacting a compound of formula

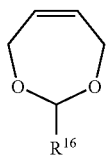

XXIV with $N_2CHCO_2R^4$ in the presence of $Rh_2(OAc)_4$. A convenient solvent is pentane.

Compounds of formula (II) in which $R^1$ represents $(CH_2)_nY$ in which n is 1 or 2 and Y is $OCONHR^3$ may be prepared by reacting a corresponding compound of formula (II) in which Y is OH with an isocyanate of formula $R^3NCO$ in the presence of a base, such as pyridine or 4-dimethylaminopyridine. Convenient solvents include an excess of the base and halogenated hydrocarbons, such as methylene chloride. The reaction is conveniently conducted at a temperature in the range of from 0 to 100° C.

Compounds of formula (II) in which $R^1$ represents $(CH_2)_nY$ in which n is 1 or 2 and Y is $NHCONHR^3$ may be prepared by reacting a corresponding compound of formula (II) in which Y is $N_3$ with an isocyanate of formula $R^3NCO$ in the presence of hydrogen and a Group VIII metal catalyst such as platinum oxide. Convenient solvents include esters such as ethyl acetate. The reaction is conveniently conducted at a temperature in the range of from 0 to 100° C. Compounds of formula (II) in which Y is $N_3$ may be prepared by reacting a corresponding compound of formula (II) in which Y is OH with diethylazodicarboxylate and a triarylphosphine such as triphenylphosphine, followed by diphenylphosphoryl azide. Convenient solvents include ethers, such as tetrahydrofuran. The reaction is conveniently effected at a temperature in the range of from −50° C. to 100° C.

Compounds of formula (II) in which $R^1$ represents $(CH_2)_nY$ in which n is 1 or 2 and Y is $NHCOOR^3$ may be prepared by reacting a corresponding compound of formula (II) in which Y is $N_3$ with a compound of formula $R^3OCOCl$ in the presence of hydrogen and a Group VIII metal catalyst such as platinum oxide. Convenient solvents include esters, such as ethyl acetate. The reaction is conveniently effected at a temperature in the range of from 0 to 100° C.

Compounds of formula (II) in which $R^1$ represents $(CH_2)_nY$ in which n is 1 or 2 and Y is $NHSO_2R^2$ may be prepared by reacting a corresponding compound of formula (II) in which Y is $N_3$ with hydrogen in the presence of a Group VIII metal catalyst such as platinum oxide, followed by in situ treatment with a compound of formula $R^2SO_2Cl$. Convenient solvents include esters, such as ethyl acetate. The reaction is conveniently effected at a temperature in the range of from 0 to 100° C.

Compounds of formula (II) in which $R^1$ represents $(CH_2)_nY$ in which n is 1 or 2 and Y is $NHCSNHR^3$ may be prepared by reacting a corresponding compound of formula (II) in which Y is $N_3$ with hydrogen in the presence of a Group VIII metal catalyst such as platinum oxide, followed by in situ treatment with a compound of formula $R^3NCS$. Convenient solvents include esters, such as ethyl acetate. The reaction is conveniently effected at a temperature in the range of from 0 to 100° C.

The compounds of formula (III) may be prepared by reacting a compound of formula

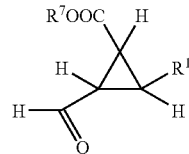

XXV with an alkali metal cyanide, such as lithium, sodium or potassium cyanide, and ammonium carbonate in an aqueous alcohol, such as aqueous ethanol. Conveniently the reaction is performed at a temperature of from 35° C. to 150° C. If desired, the compounds of formula (III) may then be alkylated, for example using a compound of formula $R^8Cl$ or $R^9Cl$. The alkylated compounds are readily separated into their diastereomers.

Compounds of formula (IV) may be prepared by reacting a compound of formula (XXV), in which $R^{10}$ is as defined for $R^7$, with an alkali metal cyanide, such as lithium, sodium or potassium cyanide, and an ammonium halide, such as ammonium chloride. It has been found advantageous to perform the reaction in the presence of ultrasound. Thus, the ammonium halide and alkali metal cyanide are advantageously mixed with chromatography grade alumina in the presence of a suitable diluent, such as acetonitrile. The mixture is then irradiated with ultrasound, whereafter the compound of formula XXV is added, and the mixture is again irradiated.

The resultant mixture of diastereoisomeric aminonitriles may then be reacted with an acylating agent, such as acetyl chloride in the presence of a suitable base, for example an amine such as diisopropylamine, and in the presence of a suitable solvent such as dichloromethane, to afford a mixture of diastereomeric acylaminonitriles. The desired stereoisomer may conveniently be separated from this mixture, for example by chromatography.

The compounds of formula (XXV) may be prepared by oxidising a compound of formula

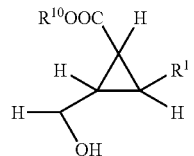

XXVI for example by a Swern oxidation.

The compounds of formula (XXVI) may be prepared by selectively deprotecting a compound of formula

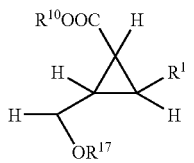

XXVII in which $R^{17}$ represent a hydroxyl protecting group, for example a benzyl group. The deprotection may be performed in a conventional manner. For example, a benzyl group may be removed by catalytic hydrogenation using palladium on charcoal as catalyst.

It will be appreciated that in order to obtain a compound of formula I which is in the configuration of formula Ia, the intermediates must be prepared in the appropriate configurations. The following formulae illustrate the respective configurations for each of the intermediates.

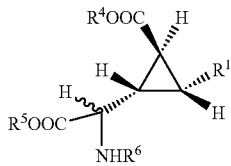

IIb

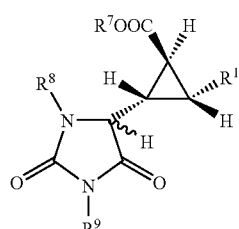

IIIb

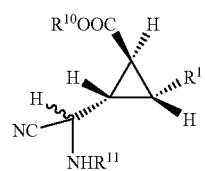

IVb

-continued

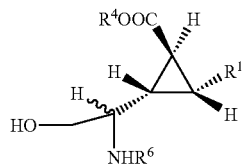

Vb

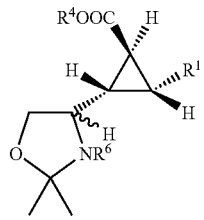

VIb

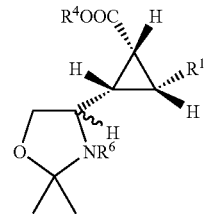

VIIb

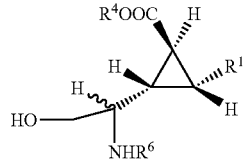

VIIIb

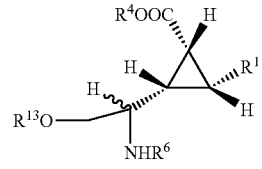

IXb

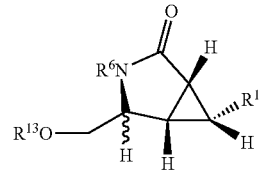

Xb

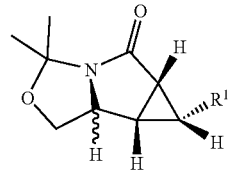

XIb

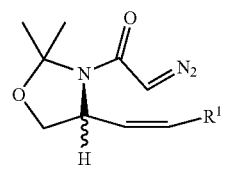

XIIb

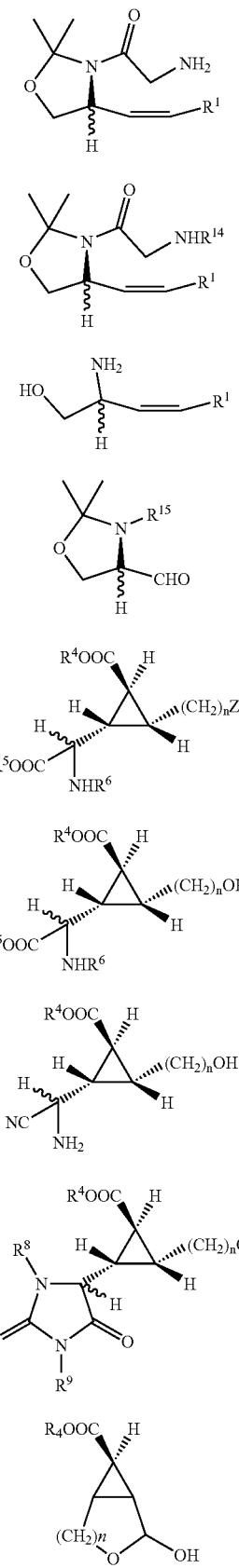
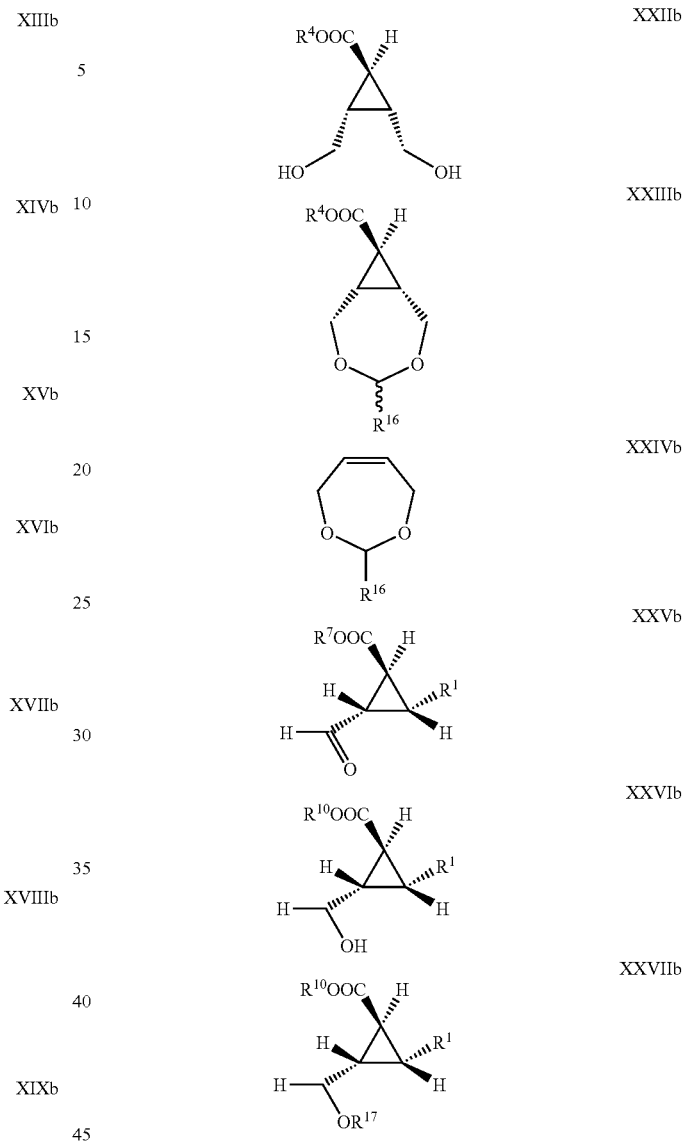

It will be appreciated that in order to obtain compounds in the configuration of formula Ib, the configuration of the amino acid group in the intermediates should be the natural configuration. This may be represented by replacing the wavy line in the formulae above with a wedge, as shown in formula Ib.

Certain of the intermediates disclosed herein, for example the compounds of formula II, are believed to be novel and are accordingly provided as further aspects of the invention.

As described hereinabove, the compounds of the invention are useful for the treatment of disorders of the central nervous system.

According to another aspect therefore, the present invention provides a method of treating a patient suffering from or susceptible to a disorder of the central nervous system, which comprises administering an effective amount of a compound of formula I as defined hereinabove, or a pharmaceutically acceptable metabolically labile ester thereof, or a pharmaceutically acceptable salt thereof.

The particular effective amount or dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

A variety of physiological functions have been shown to be subject to influence by excessive or inappropriate stimulation of excitatory amino acid transmission. The formula I compounds of the present invention are believed to have the ability to treat a variety of neurological disorders in patients associated with this condition, including acute neurological disorders such as cerebral deficits subsequent to cardiac bypass surgery and grafting, stroke, cerebral ischemia, spinal cord trauma, head trauma, perinatal hypoxia, cardiac arrest, and hypoglycemic neuronal damage. The formula I compounds are believed to have the ability to treat a variety of chronic neurological disorders, such as Alzheimer's disease, Huntington's Chorea, amyotrophic lateral sclerosis, AIDS-induced dementia, ocular damage and retinopathy, cognitive disorders, and idiopathic and drug-induced Parkinson's. The present invention also provides methods for treating these disorders which comprises administering to a patient in need thereof an effective amount of a compound of formula I or a pharmaceutically acceptable metabolically labile ester thereof, or a pharmaceutically acceptable salt thereof.

The formula I compounds of the present invention are also believed to have the ability to treat a variety of other neurological disorders in patients that are associated with glutamate dysfunction, including muscular spasms, convulsions, migraine headaches, urinary incontinence, psychosis, (such as schizophrenia), drug tolerance and withdrawal (such as nicotine, opiates and benzodiazepines), anxiety and related disorders, emesis, brain edema, chronic pain, and tardive dyskinesia. The formula I compounds are also useful as antidepressant and analgesic agents. Therefore, the present invention also provides methods for treating these disorders which comprise administering to a patient in need thereof an effective amount of the compound of formula I, or a pharmaceutically acceptable metabolically labile ester thereof, or a pharmaceutically acceptable salt thereof.

The term "treating" for purposes of the present invention, includes prophylaxis, amelioration or elimination of a named condition once the condition has been established.

The term "patient" for purposes of the present invention is defined as any warm blooded animal such as, but not limited to, a mouse, guinea pig, dog, horse, or human. Preferably, the patient is human.

According to another aspect, the present invention provides a compound of formula I as defined hereinabove, or a pharmaceutically acceptable metabolically labile ester thereof, or a pharmaceutically acceptable salt thereof, for use as a pharmaceutical.

According to yet another aspect, the present invention provides the use of a compound of formula I as defined hereinabove, or a pharmaceutically acceptable metabolically labile ester thereof, or a pharmaceutically acceptable salt thereof, for the manufacture of a medicament for treating a disorder of the central nervous system.

The ability of compounds to modulate metabotropic glutamate receptor function may be demonstrated by examining their ability to influence either cAMP production (mGluR 2, 3, 4, 6, 7 or 8) or phosphoinositide hydrolysis (mGluR 1 or 5) in cells expressing these individual human metabotropic glutamate receptor (mGluR) subtypes. (D. D. Schoepp, et al., Neuropharmacol., 1996, 35, 1661–1672 and 1997, 36, 1–11).

In these tests the compound of Example 1 of the present application was found to reverse [3H] LY341495 binding with a Ki of 285 nM at mGluR$^2$. (LY341495 is described in Ornstein et al., J. Med. Chem., 1998, 41, 346–357 and J. Med. Chem., 1998, 41, 358 to 378).

The compounds of the present invention are preferably formulated prior to administration. Therefore, another aspect of the present invention is a pharmaceutical formulation comprising a compound of formula I, a pharmaceutically acceptable metabolically labile ester thereof, or a pharmaceutically acceptable salt thereof, and a pharmaceutically-acceptable carrier, diluent, or excipient. The present pharmaceutical formulations are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 5 mg to about 500 mg, more preferably about 25 mg to about 300 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|                    | Quantity (mg/capsule) |
| ------------------ | --------------------- |
| Active Ingredient  | 250                   |
| Starch, dried      | 200                   |
| Magnesium stearate | 10                    |
| Total              | 460 mg                |

The above ingredients are mixed and filled into hard gelatin capsules in 460 mg quantities.

Formulation 2

Tablets each containing 60 mg of active ingredient are made as follows:

|                              |        |
| ---------------------------- | ------ |
| Active Ingredient            | 60 mg  |
| Starch                       | 45 mg  |
| Microcrystalline cellulose   | 35 mg  |
| Polyvinylpyrrolidone         | 4 mg   |
| Sodium carboxymethyl starch  | 4.5 mg |
| Magnesium stearate           | 0.5 mg |
| Talc                         | 1 mg   |
| Total                        | 150 mg |

The active ingredient, starch, and cellulose are passed through a No. 45 mesh U.S. (0.3 mm) sieve and mixed thoroughly. The solution of polyvinylpyrrolidone is mixed with the resultant powders which are then passed through a No. 14 mesh U.S. (1.5 mm) sieve. The granules so produced are dried at 50° C. and passed through a No. 18 mesh U.S. (1 mm) sieve. The sodium carboxymethyl starch, magnesium stearate, and talc, previously passed through a No. 60 mesh U.S. (0.2 mm) sieve, are then added to the granules which, after mixing, are compressed on a tablet machine to yield tablets each weighing 150 mg.

The following Examples illustrate the invention. In the Examples, the term "Garner's aldehyde" signifies 1,1-dimethylethyl (S) or (R)-4-formyl-2,2-dimethyl-3-oxazolidine carboxylate, $Ph_3PEtBr$ signifies (ethyl)triphenylphosphonium bromide, KHMDS and LiHMDS signify potassium and lithium bis(trimethylsilyl)amide respectively, $Et_2O$ signifies diethylether, AcOEt signifies ethyl acetate, MeOH signifies methanol, Boc signifies t-butoxycarbonyl, $Et_3N$ signifies triethylamine, THF signifies tetrahydrofuran, TMSOTf signifies trimethylsilyl trifluoromethanesulfonate, $Pd(OAc)_2$ signifies palladium acetate, DMF signifies dimethylformamide, DMAP signifies 4-dimethylaminopyridine, Jones Reagent signifies a solution of 1.og of $Na_2Cr_2O_7.2H_2O$ and 1.34 g of sulfuric acid in $H_2O$ (total volume 5 ml), DBU signifies 1,8-diazabicyclo[5.4.0]undec-7-ene and DME signifies ethylene glycol dimethyl ether.

Preparation 1

Ethyl (2SR,1'SR,2'RS,3'RS)-N-(tert-butoxycarbonyl)-2-[2'-(ethoxycarbonyl)-3'-hydroxymethyl-cyclopropyl]glycinate a) Ethyl 2,3-dihydroxymethylcyclopropane carboxylate.

To a solution of cis-4,7-dihydro-1,3-dioxepin (4.57 g, 45.6 mmol) in pentane (25 mL) under nitrogen at room temperature, $Rh_2(OAc)_4$ (220 mg, 0.5 mmol) was added. To the resulting suspension vigorously stirred, a solution of ethyl diazoacetate (10.5 mL, 100 mmol) in pentane (75 mL) was added dropwise at room temperature over a period of 3–4 hours. After the addition was completed, solvent was removed under vacuo and residue was chromatographed using a gradient of AcOEt/Hexane 1:10 to 1:5 as eluent. 6.75 g of an inseparable mixture of cyclopropanated product and $EtO_2CCH=CHCO_2Et$ was obtained. A solution of this mixture in ethanol saturated with hydrogen chloride (250 mL) was stirred overnight at room temperature. The following day, solvent was removed under vacuo and residue taken into ethanol (100 mL). This solution was neutralized with $NaHCO_3$ (solid), filtered and concentrated. The resulting residue was chromatographed using a gradient of AcOEt/Hexane 1:1 to 3:1 as eluent to give 4.3 g (56% yield) of diol. $^1$H-NMR (200 MHz, $CDCl_3$): 1.23 (t, J=7.1 Hz, 3H), 1.49 (t, J=3.5, 1H), 1.89–2.00 (m, 2H), 2.72 (br s, 2H), 3.31–3.42 (m, 2H), 4.05–4.16 (m, 2H) and 4.10 ppm (c, J=7.1 Hz, 2H). $^{13}$C-NMR (50 MHz, $CDCl_3$): 14.0, 23.8, 27.1 (2C), 60.3 (2C), 60.8 and 172.8 ppm.

b) Ethyl (1RS,5SR,6RS)-2-hydroxy-3-oxabicyclo[3.1.0]hexane-6-carboxylate

To a solution of oxalyl chloride (0.38 mL, 4.48 mmol) in $CH_2Cl_2$ (20 mL) at −78° C. under nitrogen atmosphere, dimethylsulfoxide (0.66 mL, 9.33 mmol) was added and stirred for 20 minutes. To this mixture, a solution of the product of step a) (650 mg, 3.73 mL) in $CH_2Cl_2$ was added and reaction was stirred at the same temperature for 30 minutes. Then, triethylamine (2.6 mL, 18.65 mmol) was added and mixture allowed to react at room temperature. After 30 minutes, the reaction mixture was quenched with water, the layers were separated and the aqueous layer was extracted with $CH_2Cl_2$ (2×). The combined organic layers were dried ($Na_2SO_4$), filtered and evaporated to give a residue which was chromatographed using a gradient of AcOEt/Hexane 1:2 to 1:1 as eluent to give 470 mg (73% yield) of lactol. $^1$H-NMR (200 MHz, $CDCl_3$): 1.23 (t, J=7.1 Hz, 3H), 1.43 (t, J=3.3 Hz, 1H), 2.21–2.23 (m, 2H), 2.76 (d, J=3.0 Hz, 1H), 3.85 (d, J=8.7 Hz, 1H), 4.06 (d, J=8.7 Hz, 1H), 4.10 (c, J=7.1 Hz, 2H) and 5.32 (d, J=3.0 Hz, 1H). $^{13}$C-NMR (50 MHz, $CDCl_3$): 14.1, 22.1, 25.0, 31.2, 60.8, 67.3, 97.8 and 171.9 ppm.

c) (2SR) and (2RS)-2-(1'SR,2'RS,3'RS)-2'-(ethoxycarbonyl)-3'-hydroxymethylcyclopropyl]glycinonitrile.

A suspension of ammonium chloride (2.42 g, 45.3 mmol) and neutral aluminium oxide (1.4 g) in acetonitrile (50 mL) was ultrasonicated for one hour. A solution of the product of step b) (780 mg, 4.53 mmol) in acetonitrile (20 mL) was then added and ultrasonicated for one hour. After potassium cyanide (3.54 g, 54.36 mmol) finely powdered was added, the mixture was allowed to react for 15 hours. Then, additional aluminium oxide (3.2 g) was added and the reaction mixture was ultrasonicated for 4 days. The mixture was then filtered through celite and the inorganics washed with acetonitrile to give 710 mg (78% yield) of the four possible aminonitriles as a yellow oil.

d) (Alternative 1) Ethyl (2SR,1'SR,2'RS,3'RS)-N-(tert-butoxycarbonyl)-2-[2'-(ethoxycarbonyl)-3'-hydroxymethyl-cyclopropyl]glycinate A solution of the product of step c) (380 mg, 1.92 mmol) in ethanol saturated with hydrogen chloride (20 mL) and $H_2O$ (0.10 mL, 5.75 mmol) was stirred for one hour at 0° C. and for 48 hours at room temperature. The following day, the solvent was removed in vacuo and the residue was dissolved in ethanol (25 mL). Then, the solution was neutralized with NaHCO₃ (solid), filtered through celite and concentrated to dryness. The resulting residue was taken into dioxane (20 mL), and a saturated aqueous solution of NaHCO₃ (5 mL) was added. Then, a solution of di-tert-butyldicarbonate (500 mg, 2.3 mmol) in dioxane (5 mL) was added and mixture stirred overnight. The layers were then separated and the aqueous layer was extracted with ethyl acetate (AcOEt). The combined organic layers were dried (Na₂SO₄), filtered and concentrated to dryness. The residue was purified by column chromatography using AcOEt/Hexane 1:2 as eluent to give 400 mg of a 1:2 mixture of diastereoisomers (61% overall yield). The minor and desired isomer (lower Rf) was separated by column chromatography using AcOEt/Hexane 1:3 as eluent giving rise to ethyl (2SR,1'SR,2'RS,3'RS)-N-(tert-butoxycarbonyl)-2-[2'-(ethoxycarbonyl)-3'-hydroxymethyl-cyclopropyl]glycinate as a mixture of enantiomers.

d) (Alternative 2) Ethyl (2SR,1'SR,2'RS,3'RS)-N-(tert-butoxycarbonyl)-2-[2'-(ethoxycarbonyl)-3'-hydroxymethylcyclopropyl]glycinate A solution of the product of step b) (1.8 g, 10.45 mmol) in EtOH (65 mL) and NaOH(1N) (63 mL, 63.0 mmol) was stirred at 60° C. for 1 hour. The mixture was then cooled to 0° C. and the pH was adjusted to ~6 by addition of 1N KHSO₄. To the resulting solution, (NH₄)₂CO₃ (10.1 g, 104.5 mmol) and NaCN (1.02 g, 20.9 mmol) were added. The mixture was stirred under reflux overnight (16–17 hours) and then cooled to room temperature. The solution was then evaporated to dryness under vacuo to give a residue that was taken into MeOH and filtered off. The inorganics were washed with MeOH and the combined methanolic filtrates were concentrated in vacuo. The resulting residue was dissolved in 1N NaOH (200 mL) and the mixture was stirred under reflux for 48 hours and then cooled to 0° C. The pH was then adjusted to 1–2 by addition of 1N HCl, and the solvent was removed under vacuo.

The resulting residue was dissolved in a 1N HCl/ethanol solution (250 mL) and the mixture was stirred overnight at room temperature. The solvent was then removed under vacuo and the residue was taken into EtOH (200 mL). After the solvent was removed under vacuo, the residue was again taken into EtOH (200 mL) and the solution neutralized with NaHCO₃ (solid), the inorganics filtered off and the filtrate concentrated to dryness. The residue was taken into dioxane (200 mL) at room temperature and a saturated aqueous solution of NaHCO₃ (50 mL) was added. Then, a solution of di-tert-butyldicarbonate (2.75 g, 12.54 mmol) in dioxane (50 mL) was added dropwise and the mixture was vigorously stirred at room temperature overnight. The mixture was then diluted with AcOEt and the layers were separated. The aqueous layer was extracted with AcOEt (2×) and the combined organic layers were dried (Na₂SO₄), filtered and concentrated to dryness. The residue was purified by column chromatography using AcOEt/hexane (1:2) as eluent to give 2.15 g of a 2.3:1 mixture of diastereoisomers (60% overall yield). The major and desired isomer (lower Rf) was separated by column chromatography using Et₂O/Hexane 1:1 as eluent giving rise to ethyl (2SR,1'SR,2'RS,3'RS)-N-(tert-butoxycarbonyl)-2-[2'-(ethoxycarbonyl)-3'-hydroxymethyl-clopropyl]glycinate as a mixture of enantiomers.

¹H-NMR (200 MHz, CDCl₃): 1.25 (t, J=7.1 Hz, 3H), 1.32 (t, J=7.1 Hz, 3H), 1.45 (s, 9H), 1.70–1.81 (m, 2H), 1.91–2.11 (m, 1H), 3.17 (dd, J=3.1, 10.1 Hz, 1H), 3.54–3.67 (m, 1H), 3.95–4.33 (m, 6H), and 5.20 (br d, J=7.3 Hz, 1H).

¹³C-NMR (50 MHz, CDCl₃): 14.0, 14.1, 22.5, 28.2 (3C), 28.9, 29.2, 52.3, 60.8, 61.0, 62.5, 80.4, 155.3, 171.8 and 172.4 ppm.

EXAMPLES 1–5

(2SR,1'SR,2'RS,3'RS)-2-(3'-substituted carbamoyloxymethyl-2'-carboxycyclopropyl)glycines The compounds of Examples 1 to 5 were prepared by the following general procedure:

a) Ethyl (2SR,1'SR,2'RS,3'RS)-N-(tert-butoxycarbonyl)-2-[2'-(ethoxycarbonyl)-3'-substituted carbamoyloxymethylcyclopropyl]glycinates Two equivalents (2.8 mmol) of the corresponding isocyanate were added to a 0.1M solution of ethyl (2SR,1'SR,2'RS,3'RS)-N-(tert-butoxycarbonyl)-2-[2'-(ethoxycarbonyl)-3'-hydroxymethyl-cyclopropyl]glycinate (500 mg, 1.4 mmol) in pyridine at room temperature and the mixture was stirred for two days. EtOAc and H₂O were added, the organic layer was separated and the aqueous layer was extracted with EtOAc (3×). The combined organic layers were washed with H₂O (5×), dried over MgSO₄, filtered and concentrated under vacuum. The corresponding 3'-substituted carbamoyloxymethylcyclopropylglycinates were purified by column chromatography using a 2/1 hexane/EtOAc mixture as eluent.

b) (2SR,1'SR,2'RS,3'RS)-2-(3'-substituted carbamoyloxymethyl-2'-carboxycyclopropyl)glycines A 2.5M solution of LiOH.H₂O (40 eq) in H₂O was added to a 0.1M solution of the corresponding compound from step a) in THF and the mixture was stirred at room temperature overnight. EtOAc was added, the organic layer was separated and the aqueous layer was washed with EtOAc (3×). The aqueous layer was acidified to pH 1 with 1N HCl and extracted in EtOAc (5×). The combined organic layers were dried over MgSO₄, filtered and concentrated under vacuum. The residue was dissolved in a 1N solution of HCl in EtOAc and the solution (0.12N) was stirred overnight at room temperature. It was then concentrated under vacuum and the resulting solid was washed with Et₂O. The final aminoacids were isolated as zwitterions by ion exchange chromatography.

EXAMPLE 1 a)-[2'-(ethoxycarbonyl Ethyl (2SR,1'SR,2'RS,3'RS)-N-(tert-butoxy-carbonyl)-2)-3'-phenylcarbamoyloxymethylcyclopropyl]glycinate (Yield: 70%)

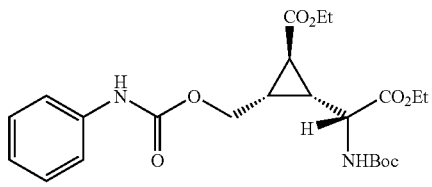

¹H-NMR (CDCl₃, 200 MHz) δ ppm): 7.6 (1H, s), 7.4 (2H, d, J=8 Hz), 7.3 (2H, dd, J=8, 7 Hz), 7.0 (1H, t, J=7 Hz), 5.5 (1H, d, J=8 Hz), 4.6 (1H, dd, J=12, 5 Hz), 4.4–4.1 (6H, m), 2.1–1.7 (3H, m), 1.5 (9H, s), 1.3–1.2 (6H, m)

¹³C-NMR (CDCl₃, 50 MHz) δ ppm): 172.6, 171.1, 155.4, 153.0, 138.0, 128.9, 123.1, 118.4, 80.2, 61.8, 60.9, 60.3, 51.7, 29.2, 28.1, 25.5, 22.6, 14.0 b) (2SR,1'SR,2'RS,3'RS)-2-(3'-phenylcarbamoyloxymethyl-2'-carboxycyclopropyl)glycine
(Yield: 55%)

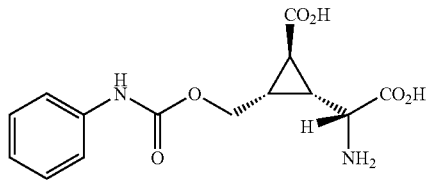

¹H-NMR (D₂O/py-d₅, 200 MHz) δ ppm): 7.0 (2H, d, J=8 Hz), 6.9 (2H, dd, J=8, 7 Hz), 6.6 (1H, t, J=7 Hz), 4.3 (1H, dd, J=12, 5 Hz), 3.9 (1H, dd, J=12, 7 Hz), 3.4 (1H, d, J=10 Hz), 1.8–1.6 (3H, m)

¹³C-NMR (D₂O/py-d₅, 50 MHz) δ ppm): 179.6, 172.7, 154.8, 137.3, 129.0, 123.2, 119.3, 63.4, 54.3, 26.7, 24.8, 23.8

EXAMPLE 2 a) Ethyl (2SR,1'SR,2'RS,3'RS)-N-(tert-butoxy-carbonyl)-2-[2'-(ethoxycarbonyl)-3'-benzylcarbamoyloxymethylcyclopropyl]glycinate
(Yield: 30%)

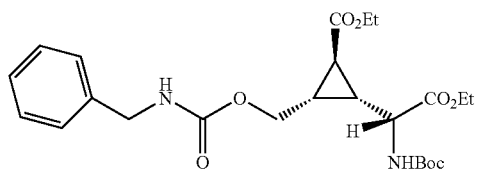

¹H-NMR (CDCl₃, 200 MHz) δ ppm): 7.3–7.2 (5H, m), 5.6 (1H, broad s), 5.5 (1H, d, J=8 Hz), 4.5 (1H, dd, J=11, 4 Hz), 4.3 (2H, d, J=6 Hz), 4.2–4.0 (6H, m), 2.0–1.7 (3H, m), 1.4 (9H, s), 1.2 (6H, dt, J=7 Hz)

¹³C-NMR (CDCl₃, 50 MHz) δ ppm): 172.4, 170.9, 155.9, 154.6, 138.3, 128.3, 127.2, 127.1, 79.8, 62.1, 61.5, 60.7, 51.7, 44.7, 28.9, 28.0, 25.4, 22.9, 13.9 b) (2SR,1'SR,2'RS,3'RS)-2-(3'-benzylcarbamoyloxymethyl-2'-carboxycyclopropyl)glycine
(Yield: 50%)

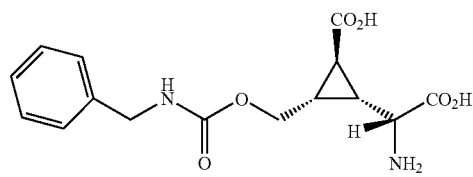

¹H-NMR (D₂O, 200 MHz) δ ppm): 7.4–7.2 (5H, s), 4.4 (1H, dd, J=12, 6 Hz), 4.3 (2H, s), 4.1 (1H, dd, J=12, 8 Hz), 3.5 (1H, d, J=10 Hz), 2.0–1.7 (3H, m)

¹³C-NMR (D₂O/MeOH-d₄, 50 MHz) δ ppm): 178.2, 172.7, 158.3, 128.8, 127.4, 126.9, 63.4, 54.3, 44.1, 26.2, 25.8, 25.3

EXAMPLE 3 a) Ethyl (2SR,1'SR,2'RS,3'RS)-N-(tert-butoxy-carbonyl)-2-[2'-(ethoxycarbonyl)-3'-ethylcarbamoyloxymethylcyclopropyl]glycinate
(Yield: 40%)

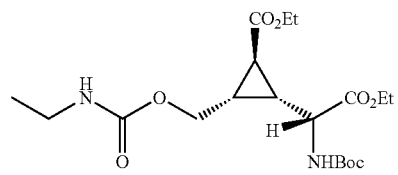

¹H-NMR (CDCl₃, 200 MHz) δ ppm): 5.5 (1H, d, J=8 Hz), 5.2 (1H, broad s), 4.4 (1H, dd, J=11, 4 Hz), 4.2–4.0 (6H, m), 3.1 (2H, m), 2.0–1.7 (3H, m), 1.4 (9H, s), 1.3–1.1 (6H, m), 1.0 (3H, t, J=7 Hz)

¹³C-NMR (CDCl₃, 50 MHZ) δ ppm): 172.4, 170.7, 155.7, 155.0, 79.8, 61.5, 60.6, 51.8, 35.5, 28.8, 27.9, 25.5, 22.9, 14.9, 13.8 b) (2SR,1'SR,2'RS,3'RS)-2-(3'-ethylcarbamoyloxymethyl-2'-carboxycyclopropyl)glycine
(Yield: 47%)

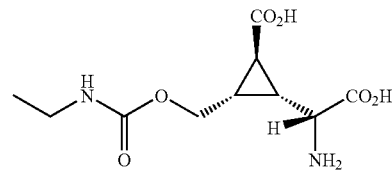

¹H-NMR (D₂O/py-ds, 200 MHz) δ ppm): 4.0 (1H, dd, J=12, 5 Hz), 3.7 (1H, dd, J=12, 7 Hz), 3.2 (1H, d, J=10 Hz), 2.6 (2H, q, J=8 Hz), 1.6–1.4 (3H, m), 0.6 (3H, t, J=8 Hz)

¹³C-NMR (D₂O/MeOH-d₄, 50 MHz) δ ppm): 179.7, 173.2, 158.0, 63.4, 54.6, 35.5, 26.9, 25.9, 24.6, 14.2

EXAMPLE 4 a) Ethyl (2SR,1'SR,2'RS,3'RS)-N-(tert-butoxy-carbonyl)-2-[2'-(ethoxycarbonyl)-3'-cyclohexylcarbamoyloxymethyl-cyclopropyl]glycinate
(Yield: 20%)

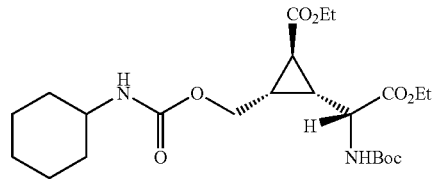

¹H-NMR (CDCl₃, 200 MHz) δ ppm): 5.4 (1H, d, J=8 Hz), 5.0 (1H, broad s), 4.5 (1H, dd, J=11, 4 Hz), 4.3–4.0 (6H, m), 3.5–3.3 (1H, m), 2.0–1.1 (19H, m), 1.4 (9H, s)

¹³C-NMR (CDCl₃, 50 MHz) δ ppm): 172.5, 171.1, 155.1, 80.0, 61.7, 60.8, 51.8, 49.7, 33.2, 29.1, 28.1, 25.7, 25.4, 24.6, 22.8, 14.0 b) (2SR,1'SR,2'RS,3'RS)-2-(3'-cyclohexylcarbamoyloxymethyl-2'-carboxycyclopropyl)glycine (Yield: 51%)

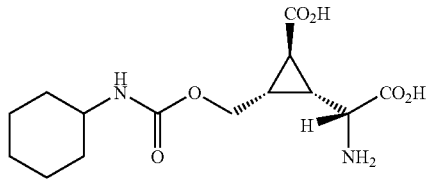

¹H-NMR (D₂O, 200 MHz) δ ppm): 4.1 (1H, dd, J=15, 5 Hz), 3.7 (1H, dd, J=13, 7 Hz), 3.2 (1H, d, J=10 Hz), 2.9 (1H, m), 1.7–0.6 (13H, m)

¹³C-NMR (D₂O/MeOH-d₄, 50 MHz) δ ppm): 180.5, 174.0, 158.4, 64.4, 55.7, 51.0, 33.6, 28.1, 27.0, 26.1, 25.8, 25.6

EXAMPLE 5 a) Ethyl (2SR,1'SR,2'RS,3'RS)-N-(tert-butoxy-carbonyl)-2-[2'-(ethoxycarbonyl)-3'-(1-naphthyl)carbamoyloxymethylcyclopropyl]glycinate (Yield: 60%)

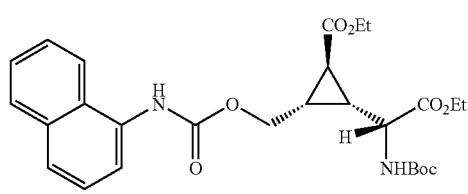

¹H-NMR (CDCl₃, 200 MHz) δ ppm): 8.1–7.0 (8H, m), 5.6 (1H, d, J=9 Hz), 4.7 (1H, dd, J=12, 5 Hz), 4.5–4.3 (2H, m), 4.24.0 (4H, m), 2.2–1.8 (3H, m), 1.5 (9H, s), 1.3–1.2 (6H, m)

¹³C-NMR (CDCl₃, 50 MHz) δ ppm): 172.5, 171.0, 155.3, 153.6, 133.8, 132.5, 128.3, 125.8, 125.7, 125.5, 124.4, 120.7, 118.3, 79.9, 61.7, 60.7, 60.1, 51.5, 29.2, 28.0, 25.3, 22.2, 13.9 b) (2SR,1'SR,2'RS,3'RS)-2-[3'-(1-naphthyl)carbamoyloxymethyl-2'-carboxycyclopropyl]glycine (Yield: 53%)

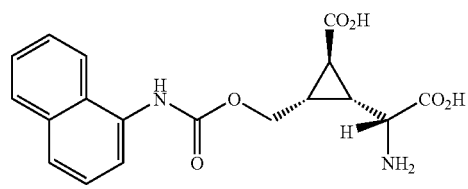

¹H-NMR (D₂O, 200 MHz) δ ppm): 7.6–7.0 (7H, m), 4.3 (1H, dd, J=10, 5 Hz), 3.9 (1H, m), 3.3 (1H, d, J=10 Hz), 1.8–1.5 (3H, m)

¹³C-NMR (D₂O/MeOH-d₄, 50 MHz) δ ppm): 179.3, 173.3, 157.1, 134.1, 132.3, 128.5, 126.8, 126.7, 125.9, 122.7, 122.2, 64.2, 54.6, 26.7, 26.2, 25.1

EXAMPLE 6

(2SR,1'SR,2'RS,3'RS)-2-[3'-(3-methoxy)phenylcarbamoyloxymethyl-2'-carboxycyclopropyl]glycine

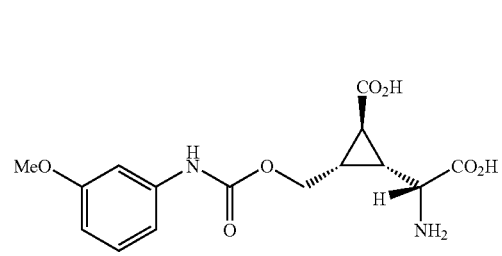

To a solution of ethyl (2SR,1'SR,2'RS,3'RS)-N-(tert-butoxycarbonyl)-2-[2'-(ethoxycarbonyl)-3'-hydroxymethylcyclopropyl]glycinate (100 mg, 0.29 mol) in methylene chloride (3 mL) the corresponding aryl isocyanate (1.16 mmol) and 4-dimethylaminopyridine (0.35 mmol, 43 mg) were added at room temperature. The mixture was stirred for 48 h and then concentrated under vacuum. The residue was dissolved in THF (1 mL) and a solution of LiOH.H₂O (11.6 mmol, 0.12 g) in H₂O (1.2 mL) was added, the mixture was stirred at room temperature for 16 h and then the THF was concentrated under vacuum. EtOAc (3 mL) was added, the organic layer separated by freezing the aqueous layer, and the aqueous layer was washed with EtOAc and then acidified to pH1 by addition of 1N HCl. The mixture was then extracted in EtOAc (3×) and the combined organic layers were dried over MgSO₄, filtered and concentrated under vacuum. A 1N solution of HCl (g) in EtOAc (2 mL) was added and the mixture stirred at room temperature overnight. The mixture was then concentrated under vacuum and the solid residue washed with diethyl ether and dried. The title compound was isolated by Dowex chromatography. Yield 18%.

¹³C-NMR (D₂O/py-d5, 50 MHz) δ ppm): 179.3, 173.1, 159.6, 154.8, 139.7, 129.9, 111.6, 108.8, 104.6, 64.0, 55.1, 54.9, 27.9. 26.2, 24.6

EXAMPLES 7–9

(2SR,1'SR,2'SR,3'RS)-2-(3'-substituted ureidomethyl-2'-carboxycyclopropyl)glycines The compounds of Examples 7 to 9 were prepared by the following general procedure:

a) Ethyl (2SR,1'SR,2'SR,3'RS)-N-(tert-butoxycarbonyl)-2-[2'-(ethoxycarbonyl)-3'-azidomethylcyclopropyl]glycinate

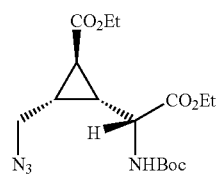

Diethyl azodicarboxylate (1.08 mmol, 0.17 mL) was added to a solution of triphenylphosphine (1.08 mmol, 0.285 g) in anhydrous THF (20 mL) under nitrogen at −20° C. and the reaction mixture was stirred at the same temperature for 10 min. A solution of ethyl (2SR,1'SR,2'RS,3'RS)-N-(tert-butoxycarbonyl)-2-[2'-(ethoxycarbonyl)-3'-hydroxymethylcyclopropyl]glycinate (0.87 mmol, 300 mg) in THF (5 mL) was added and the resulting mixture stirred for 10 min at −20° C. Diphenylphosphoryl azide (1.13 mmol, 0.25 mL) was added at the same temperature and the reaction mixture was allowed to react at room temperature for 3 days. The reaction mixture was quenched with water, extracted in EtOAc, and the combined organic layers dried over magnesium sulfate, filtered and concentrated under vacuum. The residue was purified by column chromatography using a 4/1 hexane/EtOAc mixture as eluent. (Yield: 78%)

$^1$H-NMR (CDCl$_3$, 200 MHz) δ ppm: 5.2 (1H, d, J=8 Hz), 4.3–3.9 (5H, m), 3.6 (1H, dd, J=13, 5 Hz), 3.4 (1H, dd, J=13, 7 Hz), 1.9–1.7 (3H, m), 1.4 (9H, s), 1.3–1.2 (6H, m)

$^{13}$C-NMR (CDCl$_3$, 50 MHz) δ ppm: 172.1, 170.7, 155.2, 80.2, 61.8, 61.0, 52.0, 49.4, 29.0, 28.1, 25.4, 24.0, 14.0 b) Ethyl (2SR,1'SR,2'SR,3'RS)-N-(tert-butoxycarbonyl)-2-[2'-(ethoxycarbonyl)-3'-substituted ureidomethylcyclopropyl]glycinate To a solution of ethyl (2SR,1'SR,2'SR,3'RS)-N-(tert-butoxycarbonyl)-2-[2'-(ethoxycarbonyl)-3'-azidomethylcyclopropyl]glycinate (1.35 nmol, 500 mg) in EtOAc (15 mL), 2 equivalents of the corresponding isocyanate (2.7 mmol) and 0.2 equivalents of PtO$_2$ (0.27 mmol, 60 mg) were added and the mixture was stirred at room temperature under H$_2$ for 4 hours. The mixture was filtered through celite and concentrated under vacuum. The residue was chromatographed using a 2/1 hexane/EtOAc mixture as eluent giving rise to the pure product.

c) (2SR,1'SR,2'SR,3'RS)-2-(3'-substituted ureidomethyl-2'-carboxycyclopropyl)glycine A 2.5M solution of LiOH.H$_2$O (40 eq) in H2O was added to a 0.1M solution of the product of step b) in THF and the mixture was stirred at room temperature overnight. EtOAc was added, the organic layer was separated and the aqueous layer was washed with EtOAc (3×). The aqueous layer was acidified to pH 1 with 1N HCl and extracted in EtOAc (5×). The combined organic layers were dried over MgSO$_4$, filtered and concentrated under vacuum. The residue was dissolved in a 1N solution of HCl in EtOAc and the solution (0.12N) was stirred overnight at room temperature. It was then concentrated under vacuum and the resulting solid was washed with Et$_2$O. The final aminoacid was isolated as a zwitterion by ion exchange chromatography.

EXAMPLE 7 b) Ethyl (2SR,1'SR,2'SR,3'RS)-N-(tert-butoxy-carbonyl)-2-[2'-(ethoxycarbonyl)-3'-phenylureidomethylcyclopropyl]glycinate (Yield: 63%)

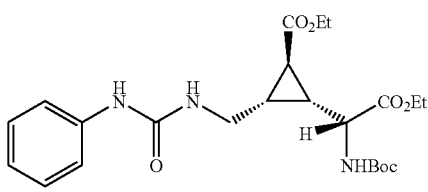

$^1$H-NMR (CDCl$_3$, 200 MHz) δ ppm: 7.5–7.2 (5H, m), 7.1–7.0 (1H, m), 5.9 (1H, t, J=6 Hz), 5.4 (1H, d, J=8 Hz), 4.2–4.0 (5H, m), 3.8–3.7 (1H, m), 3.3–3.1 (1H, m), 2.0–1.7 (3H, m), 1.5 (9H, s), 1.3–1.2 (6H, m)

$^{13}$C-NMR (CDCl$_3$, 50 MHz) δ ppm: 172.4, 171.5, 155.7, 155.4, 138.9, 129.7, 128.9, 123.0, 120.4, 80.4, 62.0, 60.9, 52.4, 38.5, 28.9, 28.1, 27.2, 23.3, 14.0 c) (2SR,1'SR,2'SR,3'RS)-2-(3'-phenylureidomethyl-2'-carboxycyclopropyl)glycine (Yield 56%)

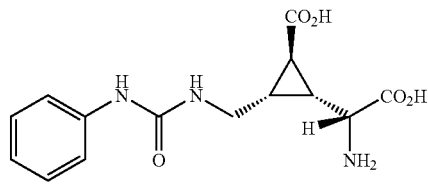

$^1$H-NMR (D$_2$O, 200 MHz) δ ppm: 7.6–7.0 (7H, m), 4.3 (1H, dd, J=10, 5 Hz), 3.9 (1H, m), 3.3 (1H, d, J=10 Hz), 1.8–1.5 (3H, m)

$^{13}$C-NMR (D$_2$O/py-d$_5$, 50 MHz) δ ppm: 180.1, 173.4, 157.7, 138.2, 129.1, 123.7, 120.9, 54.3, 38.7, 26.8, 26.1, 25.8

EXAMPLE 8 b) Ethyl (2SR,1'SR,2'SR,3'RS)-N-(tert-butoxycarbonyl)-2-[2'-(ethoxycarbonyl)-3'-ethylureidomethylcyclopropyl]glycinate (Yield: 64%)

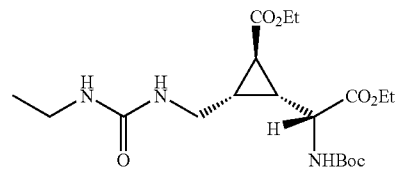

$^{13}$C-NMR (CDCl$_3$, 50 MHz) δ ppm: 172.3, 171.5, 158.2, 155.3, 79.7, 61.6, 60.5, 52.4, 38.5, 34.8, 28.7, 28.0, 27.3, 23.3, 15.2, 13.8 c) (2SR,1'SR,2'SR,3'RS)-2-(3'-ethylureidomethyl-2'-carboxycyclopropyl)glycine (Yield: 42%)

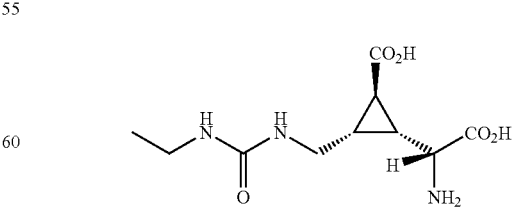

$^{13}$C-NMR (D$_2$O, 50 MHz) δ ppm: 177.6, 172.8, 53.7, 38.4, 34.9, 26.7, 26.7, 24.6, 14.2

EXAMPLE 9 b) Ethyl (2SR,1'SR,2'SR,3'RS)-N-(tert-butoxycarbonyl)-2-[2'-(ethoxycarbonyl)-3'-benzylureidomethylcyclopropyl]glycinate (Yield: 45%)

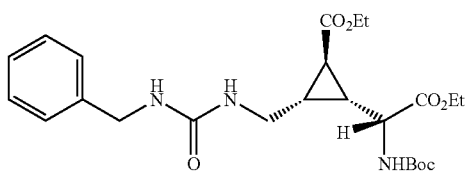

$^{13}$C-NMR (CDCl$_3$, 50 MHz) δ ppm): 172.4, 171.6, 158.0, 155.4, 139.5, 128.4, 127.3, 127.0, 80.3, 61.9, 60.7, 52.7, 44.2, 38.7, 28.9, 28.1, 27.3, 23.3, 13.9 c) (2SR,1'SR,2'SR,3'RS)-2-(3'-benzylureidomethyl-2'-carboxycyclopropyl)glycine (Yield 30%)

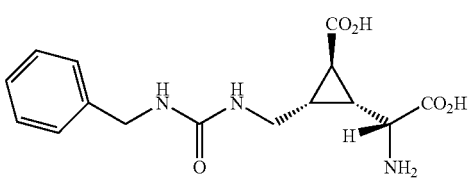

$^{13}$C-NMR (D$_2$O/py-d$_5$, 50 MHz) δ ppm): 174.2, 172.5, 157.3, 139.3, 128.3, 126.8, 126.8, 53.6, 43.2, 38.2, 27.5, 27.3, 23.5

EXAMPLE 10

(2SR,1'SR,2'SR,3'RS)-2-(3'-benzenesulfonylamuinomethyl-2'-carboxycyclopropyl)glycine a) Ethyl (2SR,1'SR,2'SR,3'RS)-N-(tert-butoxycarbonyl)-2-[2'-(ethoxycarbonyl)-3'-benzenesulfonylaminomethylcyclopropyl]glycinate

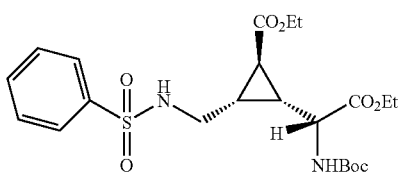

To a solution of ethyl (2SR,1'SR,2'SR,3'RS)-N-(tert-butoxycarbonyl)-2-[2'-(ethoxycarbonyl)-3'-azidomethylcyclopropyl]glycinate (1.35 mmol, 500 mg) in EtOAc (15 mL), 0.2 equivalents of PtO$_2$ (0.27 mmol, 60 mg) were added and the mixture was stirred at room temperature under H$_2$ for 4 hours. Then, 2 equivalents of benzenesulfonyl chloride (2.7 mmol) were added and the mixture was stirred under nitrogen overnight. The mixture was filtered through celite and concentrated under vacuum. The residue was chromatographed using a 2/1 hexane/EtOAc mixture as eluent giving rise to the pure product. (Yield: 56%)

$^1$H-NMR (CDCl$_3$, 200 MHz) δ ppm): 7.8 (2H, m), 7.5 (3H, m), 5.8 (1H, dd, J=9, 3 Hz), 5.2 (1H, d, J=8 Hz), 4.3–4.0 (4H, m), 3.8 (1H, m), 3.5 (1H, m), 2.8 (1H, m) 1.9–1.6 (3H, m), 1.4 (9H, s), 1.3–1.1 (6H, m)

$^{13}$C-NMR (CDCl$_3$, 50 MHz) δ ppm): 171.7, 171.1, 155.1, 140.0, 132.3, 128.9, 126.6, 80.0, 62.1, 60.7, 52.0, 41.9, 28.8, 27.9, 26.1, 23.2, 13.8, 13.7 b)(2SR,1'SR,2'SR,3'RS)-2-(3'-benzenesulfonylaminomethyl-2'-carboxycyclopropyl)glycine

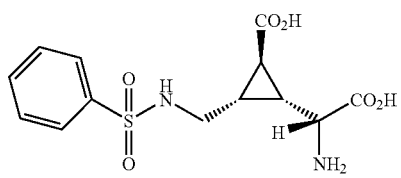

A 2.5M solution of LiOH.H$_2$O (40 eq) in H$_2$O was added to a 0.1M solution of the product of step a) in THF and the mixture was stirred at room temperature overnight. EtOAc was added, the organic layer was separated and the aqueous layer was washed with EtOAc (3×). The aqueous layer was acidified to pH 1 with 1N HCl and extracted in EtOAc (5×). The combined organic layers were dried over MgSO$_4$, filtered and concentrated under vacuum. The residue was dissolved in a 1N solution of HCl in EtOAc and the solution (0.12N) was stirred overnight at room temperature. It was concentrated under vacuum and the resulting solid was washed with Et$_2$O. The final aminoacid was isolated as a zwitterion by ion exchange chromatography.

(Yield: 44%)

$^{13}$C-NMR (D$_2$O/MeOH-d$_4$, 50 MHz) δ ppm): 179.5, 173.8, 139.3, 134.6, 130.7, 127.8, 55.0, 43.3, 27.6, 27.1, 25.7

EXAMPLE 11

(2SR,1'SR,2'SR,3'RS)-2-(3'-phenylthioureidomethyl-2'-carboxycyclopropyl)glycine hydrochloride a) Ethyl (2SR,1'SR,2'SR,3'RS)-N-(tert-butoxycarbonyl)-2-[2'-(ethoxycarbonyl)-3'-phenylthioureidomethylcyclopropyl]glycinate

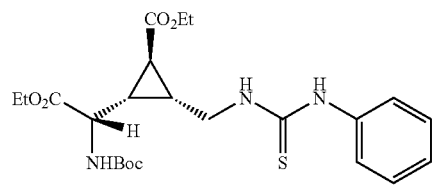

To a solution of ethyl (2SR,1'SR,2'SR,3'RS)-N-(tert-butoxycarbonyl)-2-[2'-(ethoxycarbonyl)-3'-azidomethylcyclopropyl]glycinate (1.35 mmol, 500 mg) in EtOAc (15 mL), 0.2 equivalents of PtO$_2$ (0.27 mmol, 60 mg) were added and the mixture was stirred at room temperature under H$_2$ for 4 hours. Then, 2 equivalents of phenyl isothiocyanate (2.7 mmol, 0.32 mL) were added and the reaction mixture was stirred under N$_2$ overnight. The mixture was filtered through celite and concentrated under vacuum. The residue was chromatographed using a 2/1 hexane/EtOAc mixture as eluent giving rise to the pure product. (Yield: 85%)

¹H-NMR (CDCl₃, 200 MHz) δ ppm): 7.5–7.2 (5H, m), 7.1–7.0 (1H, m), 5.2 (1H, d, J=8 Hz), 4.6 (1H, m), 4.2–3.9 (6H, m), 3.5–3.3 (1H, m), 1.9–1.6 (3H, m), 1.4 (9H, s), 1.3–1.1 (6H, m)

¹³C-NMR (CDCl₃, 50 MHz) δ ppm): 180.3, 171.9, 170.9, 155.1, 136.3, 129.4, 126.3, 124.8, 79.9, 61.5, 60.6, 52.2, 43.4, 28.8, 27.8, 25.7, 22.9, 13.8 b)(2SR,1'SR,2'SR,3'RS)-2-(3'-phenylthioureidomethyl-2'-carboxycyclopropyl)glycine hydrochloride

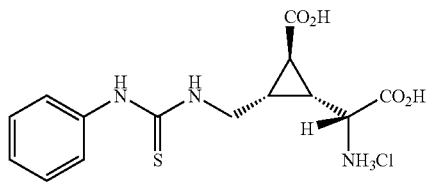

A 2.5M solution of LiOH.H₂O (40 eq) in H₂O was added to a 0.1M solution of the product of step a) in THF and the mixture was stirred at room temperature overnight. EtOAc was added, the organic layer was separated and the aqueous layer was washed with EtOAc (3×). The aqueous layer was acidified to pH 1 with 1N HCl and extracted in EtOAc (5×). The combined organic layers were dried over MgSO₄, filtered and concentrated under vacuum. The residue was dissolved in a 1N solution of HCl in EtOAc and the solution (0.12N) was stirred overnight at room temperature. It was then concentrated under vacuum and the resulting solid was washed with Et₂O to give the corresponding hydrochloride salt of the title compound. (Yield:47%)

¹³C-NMR (MeOH-d₄, 50 MHz) δ ppm): 181.7, 175.2, 170.3, 139.2, 130.2, 126.9, 125.6, 53.1, 43.8, 28.0, 27.5, 24.9

Preparation 2

Ethyl (2SR,1'SR,2'SR,3'RS)-N-(tert-butoxycarbonyl)-2-[2'-(ethoxycarbonyl)-3'-(2'-hydroxyethyl)cyclopropyl]glycinate a) Ethyl (1SR,5RS,6SR)-2-oxo-bicyclo[3.1.0]hexane-6-carboxylate To a suspension of ethyl (dimethylsulfonium)acetate bromide (13.9 g, 60.9 mmol) in chloroform (60 mL), DBU (9.18 mL, 60.9 mmol) was added. The resulting suspension was vigorously stirred at room temperature for 30 minutes. Then, cyclopentenone (5.10 mL, 60.9 mmol) was added and the mixture stirred overnight at room temperature. The following day additional chloroform (60 mL) was added. The organic layer was washed with 40 mL of 0.5 N HCl, dried over magnesium sulfate, filtered and evaporated in vacuo. The residue was purified by column chromatography using ethyl acetate:hexane 1:9 as eluent to give 8.4 g (82% yield) of ethyl (1SR,5RS,6SR)-2-oxo-bicyclo[3.1.0]hexane-6-carboxylate as a colorless oil.

¹H-NMR (300 MHz, CDCl₃): 1.22 (t, J=7.1 Hz, 3H), 1.95–2.24 (m, 6H), 2.44–2.49 (m, 1H), 4.10 (q, J=7.1 Hz, 2H).

¹³C-NMR (75 MHz, CDCl₃): 14.0, 22.3, 26.3, 29.1, 31.7, 35.6, 61.1, 170.3, 211.8 ppm.

b) Ethyl (1SR,6SR,7SR)-2-oxo-3-oxa-bicyclo[4.1.0]-heptane-7-carboxylate.

To a stirred solution of ethyl (1SR,5RS,6SR)-2-oxo-bicyclo[3.1.0]hexane-6-carboxylate (34.8 g, 207.2 mmol) in dichloromethane (300 mL), 70% m-chloroperbenzoic acid (51.1 g, 207.2 mmol) was added and refluxed overnight. The following day, additional 70% m-chloroperbenzoic acid (51.1 g, 207.2 mmol) was added and reflux continued for 15 hours. After that time, the mixture was diluted with dichloromethane (200 mL), filtered and washed with 10% Na₂SO₃ (2×200 mL) and with a saturated aqueous solution of sodium bicarbonate (2×200 mL). The organic layer was dried over magnesium sulfate, filtered and evaporated in vacuo. The residue was purified by column chromatography using ethyl acetate and hexane 1:2 as eluent to give 22.89 g (60% yield) of ethyl (1SR,6SR,7SR)-2-oxo-3-oxa-bicyclo[4.1.0]heptane-7-carboxylate as a colorless oil ¹H-NMR (300 MHz, CDCl₃): 1.24 (t, J=7.1 Hz, 3H), 1.97–2.04 (m, 1H), 2.13–2.28 (m, 3H), 2.38 (dd, J₁=8.3 Hz, J₂=3.3 Hz, 1H), 2.53 (t, J=3.9 Hz, 1H), 4.02 (td, J₁=8.8, Hz, J₂=3.3 Hz, 1H), 4.13 (q, J=7.1 Hz, 2H), 4.23–4.31 (m, 1H).

¹³C-NMR (75 MHz, CDCl₃): 14.1, 19.4, 21.4, 22.2, 24.2, 61.5, 64.3, 167.8, 170.0 ppm.

c) (2RS) and (2SR) Ethyl (1SR,6RS,7SR)-2-hydroxy-3-oxa-bicyclo[4.1.0]heptane-7-carboxylate.

To a solution of ethyl (1SR,6SR,7SR)-2-oxo-3-oxa-bicyclo[4.1.0]heptane-7-carboxylate (15.2 g, 82.8 mmol) in anhydrous tetrahydrofuran (300 mL) at −78° C. and under argon, a 1.5 M solution of diisobutylaluminium hydride in toluene (82.8 mL, 124.2 mmol) in anhydrous tetrahydrofuran (150 mL) at −78° C. under an argon atmosphere was added dropwise via cannula. The solution was stirred for six hours at this temperature and then diluted with ethyl acetate (200 mL) and quenched with a saturated aqueous solution of sodium tartrate (200 mL). The resulting mixture was stirred at room temperature overnight. The organic layer was separated, dried over magnesium sulfate, filtrated and evaporated in vacuo. The residue was purified by column chromatography using ethyl acetate and hexane 1:2 as eluent to afford 12.3 g (85% yield) of (2RS) and (2SR) ethyl (1SR,6RS,7SR)-2hydroxy-3-oxa-bicyclo[4.1.0]heptane-7-carboxylate as a colorless oil, which exist with their corresponding open hydroxyaldehyde forms.

¹H-NMR (300 MHz, CDCl₃): 1.19–1.24 (m), 1.49–1.52 (m) 1.60–1.94 (m), 2.00–2.08 (m), 2.30–2.34 (m), 2.53–2.58 (m), 3.25–3.30 (m), 3.34–3.50 (m), 3.58–3.63 (m), 3.81–3.90 (m), 4.04–4.09 (m), 5.24 ((dd, J₁=5.5 Hz, J₂=4.4 Hz), 5.29 (d, J=3.3 Hz), 9.60 (dd, J₁=3.3 Hz, J₂=1.1 Hz).

¹³C-NMR (75 MHz, CDCl₃): 13.9, 14.0, 14.1, 18.5, 20.6, 20.9, 21.0, 21.3, 23.7, 25.0, 25.7, 27.3, 28.6, 28.7, 34.8, 54.2, 59.9, 60.5, 60.6, 61.1, 61.6, 89.0, 90.0, 171.3, 173.3, 173.5 ppm.

d) (2SR) and (2RS)-2-(1'SR,2'SR,3'RS)-2'-(ethoxycarbonyl)-3'-(2''-hydroxyethyl)cyclopropyl]glycinonitrile A suspension of ammonium chloride (29.3 g, 547.3 mmol) and neutral aluminium oxide (54.7 g) in acetonitrile (600 mL), was ultrasonicated for one hour. To this mixture, a solution of (2RS) and (2SR) ethyl (1SR,6RS,7SR)-2-hydroxy-3-oxa-bicyclo[4.1.0]heptane-7-carboxylate (10.2 g, 54.7 mmol) in acetonitrile (200 mL) was added, and sonication was continued for an additional hour. Then, powdered potassium cyanide (42.8 g, 656.7 mmol) was added and reaction mixture was ultrasonicated for seven days. After that time, the mixture was filtered through celite and the inorganics washed with acetonitrile. The solvent was evaporated under reduced pressure to give a residue which contained a 1:1 racemic mixture of the two possible diastereomers. Both racemic aminonitriles were purified and separated by column chromatography using Acetone/Hexane 1:2 as eluent to give 3.89 g of (2SR,1'SR,2'SR,3'SR)-2'-(ethoxycarbonyl)-3'-(2"-hydroxyethyl)cyclopropyl]glycinonitrile and 3.67 g of (2RS,1'SR,2'SR,3'RS)-2'-(ethoxycarbonyl)-3'-(2"-hydroxyethyl)cyclopropyl]glycinonitrile.

e) Ethyl (2SR,1'SR,2'SR,3'RS)-N-(tert-butoxycarbonyl)-2-[2'-(ethoxycarbonyl)-3'-(2"-hydroxyethyl)cyclopropyl]glycinate.

To a solution of (2SR,1'SR,2'SR,3'RS)-2-[2'-(ethoxycarbonyl)-3'-(2"-hydroxyethyl)cyclopropyl]glycinonitrile (3.88 g, 18.3 mmol) in ethanol saturated with hydrogen chloride (200 mL) at 0° C., distilled water (0.99 mL, 54.9 mmol) was added. The reaction was stirred at room temperature for four days. Then, solvent was eliminated in vacuo and residue dissolved in absolute ethanol (100 mL), neutralized with NaHCO$_3$ (solid) and stirred for 30 minutes. The inorganics were filtered and the solvent was removed under reduced pressure to dryness. The resulting residue was taken into dioxan (150 mL), and a saturated aqueous solution of NaHCO$_3$ (50 mL) was added. To this mixture, a solution of di-tert-butyldicarbonate (4.80 mg, 22.8 mmol) in dioxan (25 mL) was added and mixture stirred overnight at room temperature. The layers were then separated and the aqueous layer was extracted with ethyl acetate (2×200 mL). The combined organic layers were dried over sodium sulfate, filtered and concentrated to dryness. The residue was purified by column chromatography using ethyl acetate/hexane 1:2 as eluent to afford 3.34 g (56% yield) of ethyl (2SR,1'SR,2'SR,3'RS)-N-(tert-butoxycarbonyl)-2-[2'-(ethoxycarbonyl)-3'-(2"-hydroxyethyl)cyclopropyl]glycinate as a yellow oil.

$^1$H-NMR (300 MHz, CDCl$_3$): 1.25 (t, J=7.1 Hz, 3H), 1.30 (t, J=7.1 Hz, 3H), 1.45 (s, 9H), 1.67–1.69 (m, 2H), 1.97–2.00 (m, 1H), 3.76–3.78 (m, 2H), 4.04 (t, J=9.3 Hz, 1H), 4.11 (q, J=7.1 Hz, 2H), 4.23 (q, J=7.1 Hz, 2H), 5.33 (d, J=8.2 Hz, 1H).

$^{13}$C-NMR (75 MHz, CDCl$_3$): 14.0, 14.1, 24.3, 24.8, 28.2, 29.6, 30.9, 52.1, 60.7, 61.7, 62.0, 80.1, 155.3, 171.4, 173.2 ppm.

EXAMPLE 12

(2SR,1'SR,2'SR,3'RS)-2-[(3'-(2"-phenylcarbamoyloxyethyl)-2'-carboxy)cyclopropyl]glycine hydrochloride a) Ethyl (2SR,1'SR,2'SR,3'RS)-N-(tert-butoxycarbonyl)-2-[(3'-(2"-phenylcarbamoyloxyethyl)cyclopropyl]glycinate

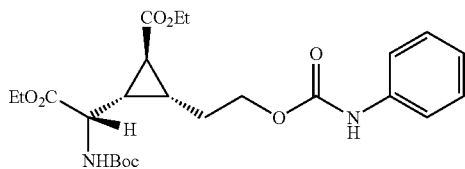

Phenyl isocyanate (2.1 mmol) was added to a 0.1M solution of ethyl (2SR,1'SR,2'SR,3'RS)-N-(tert-butoxycarbonyl)-2-[2'-(ethoxycarbonyl)-3'-(2"-hydroxyethyl)cyclopropyl]glycinate (500 mg, 1.4 nmol) in pyridine at room temperature and the mixture was stirred for two days. EtOAc and H$_2$O were added, the organic layer was separated and the aqueous layer was extracted with EtOAc (3×). The combined organic layers were washed with H$_2$O (5×), dried over MgSO$_4$, filtered and concentrated under vacuum. The corresponding product was purified by column chromatography using a 3/1 hexane/EtOAc mixture as eluent.

(Yield: 37%)

$^{13}$C-NMR (50 MHz, CDCl$_3$): 173.1, 171.1, 155.5, 153.8, 138.0, 128.3, 122.6, 118.8, 118.3, 79.7, 63.6, 61.3, 60.5, 52.0, 28.6, 27.6, 27.0, 24.4, 13.4 ppm.

b) (2SR,1'SR,2'SR,3'RS)-2-[(3'-(2"-phenylcarbamoyloxyethyl)-2'-carboxy)cyclopropyl]glycine hydrochloride

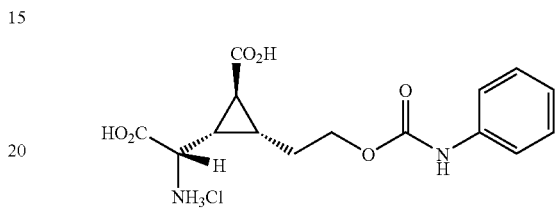

A 2.5M solution of LiOH.H$_2$O (40 eq) in H$_2$O was added to a 0.1M solution of the corresponding compound from step a) in THF and the mixture was stirred at room temperature overnight. EtOAc was added, the organic layer was separated and the aqueous layer was washed with EtOAc (3×). The aqueous layer was acidified to pH 1 with 1N HCl and extracted in EtOAc (5×). The combined organic layers were dried over MgSO$_4$, filtered and concentrated under vacuum. The residue was dissolved in a 1N solution of HCl in EtOAc and the solution (0.12N) was stirred overnight at room temperature. It was then concentrated under vacuum and the resulting solid was washed with Et$_2$O to give the corresponding hydrochloride salt of the title compound.

(Yield: 68%)

$^1$H-NMR (200 MHz, MeOH-d$_4$): 7.4 (2H, d, J=8 Hz), 7.3 (2H, dd, J=8, 7 Hz), 7.0 (1H, m), 4.3 (2H, m), 3.8 (1H, d, J=11 Hz), 2.2 (1H, m), 2.0–1.6 (4H, m)

EXAMPLE 13

(2SR,1'SR,2'SR,3'RS)-2-[(3'-(2"-phenylureidoethyl)-2'-carboxy)cyclopropyl]glycine a) Ethyl (2SR,1'SR,2'SR,3'RS)-N-(tert-butoxycarbonyl)-2-[2'-(ethoxycarbonyl)-3'-(2"-diphenylphosphoryloxyethyl) cyclopropyl]glycinate To a solution of ethyl (2SR,1'SR,2'SR,3'RS)-N-(tert-butoxycarbonyl)-2-[2'-(ethoxycarbonyl)-3'-(2"-hydroxyethyl)cyclopropyl]glycinate (100 mg, 0.28 nmol) in anhydrous toluene (2 mL) at room temperature under nitrogen atmosphere, diphenylphosphorylazide (0.053 mL, 0.33 mmol) was added. After 30 minutes, DBU was added (0.046 mL, 0.31 mmol) and the reaction mixture stirred overnight. The following day reaction mixture was quenched with water (2 mL) and aqueous phase extracted with ethyl acetate (2×2 mL). The combined organic layers were dried over magnesium sulfate, filtrated and evaporated under reduced pressure. The resulting residue was purified by column chromatography using hexane and ethyl acetate 7:3 as eluent to afford 132 mg (80% yield) of ethyl (2SR,1'SR,2'SR,3'RS)-N-(tert-butoxycarbonyl)-2-[2'-(ethoxycarbonyl)-3'-(2"-diphenylphosphoryloxyethyl)cyclopropyl]glycinate $^1$H-NMR (CDCl$_3$, 200 MHz) δ (ppm): 7.4–7.2 (10H, m), 5.2 (1H, broad s), 4.3 (2H, q, J=7 Hz), 4.2 (2H, q, J=7.2 Hz), 4.0 (2H, dd, J=1, 8 Hz, 7 Hz), 2.3–2.1 (1H, m), 1.8–1.6 (4H, m), 1.4 (9H, s), 1.2 (3H, t, J=7, 2 Hz), 1.1 (3H, t, J=7, 2 Hz)

$^{13}$C-NMR (CDCl$_3$, 200 MHz) δ (ppm): 173.9, 172.4, 151.4, 129.7, 125.2, 120.0, 119.9, 80.7, 68.2, 61.7, 60.7, 52.1, 29.5, 28.8, 28.1, 24.5, 23.7, 14.0 b) Ethyl (2SR,1'SR,2'SR,3'RS)-N-(tert-butoxycarbonyl)-2-[2'-(ethoxycarbonyl)-3'-(2"-azidoethyl)cyclopropyl]glycinate.

A solution of ethyl (2SR,1'SR,2'SR,3'RS)-N-(tert-butoxycarbonyl)-2-[2'-(ethoxycarbonyl)-3'-(2"-diphenylphosphoryloxyethyl)cyclopropyl]glycinate (445 mg 0.75 mmol) and sodium azide (98 mg, 1.5 mmol) in anhydrous dimethylformamide (7 mL) was stirred at room temperature for two days and then heated at 60° overnight. Then, the reaction was quenched with water (10 mL) and the aqueous phase was extracted with ethyl acetate (3×5 mL). The combined organic layers were washed with water (6×5 mL). The organic layer was dried over magnesium sulfate and the solvent evaporated in vacuo. The resulting residue was purified by column cromatography using hexane and ethyl acetate 8:2 as eluent to afford 216 mg (75% yield) of ethyl (2SR,1'SR,2'SR,3'RS)-N-(tert-butoxycarbonyl)-2-[2'-(ethoxycarbonyl)-3'-(2"-azidoethyl)cyclopropyl]glycinate.

$^1$H-NMR (CDCl$_3$, 200 MHz) δ(ppm): 5.2 (1H, broad s), 4.2 (2H, q, J=7, 2 Hz), 4.1 (2H, q, J=7.2 Hz), 3.9 (1H, m), 3.4 (2H, t, J=6, 6 Hz), 2.0 (1H, m), 1.7–1.6 (3H, m), 1.4 (9H, s), 1.3 (3H, t, J=7, 2 Hz), 1.2 (3H, t, J=7, 2 Hz)

$^{13}$C-NMR (CDCl$_3$, 200 MHz) δ(ppm): 172.5, 170.9, 153.9, 79.9, 61.5, 60.6, 52.0, 50.7, 29.5, 28.0, 27.5, 24.8, 13.9 c) Ethyl (2SR,1'SR,2'SR,3'RS)-N-(tert-butoxycarbonyl)-2-[(3'-(2"-phenylureidoethyl)cyclopropyl]glycinate

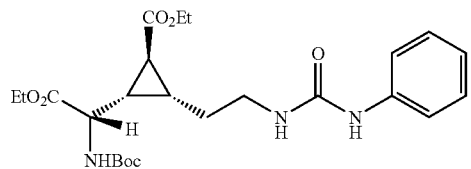

To a solution of ethyl (2SR,1'SR,2'SR,3'RS)-N-(tert-butoxycarbonyl)-2-[2'-(ethoxycarbonyl)-3'-(2"-azidoethyl)-cyclopropyl]glycinate (0.25 mmol, 95 mg) in EtOAc (3 mL), 2 equivalents of phenyl isocyanate (0.5 mmol) and 0.2 equivalents of PtO$_2$ (0.05 mmol, 11 mg) were added and the mixture was stirred at room temperature under H$_2$ for 4 hours. The mixture was filtered through celite and concentrated under vacuum. The residue was chromatographed using a 1/1 hexane/EtOAc mixture as eluent giving rise to the pure product.

(Yield: 64%)

$^{13}$C-NMR (50 MHz, CDCl$_3$): 172.9, 171.4, 155.9, 139.0, 128.9, 122.9, 119.9, 80.3, 61.8, 60.8, 52.3, 39.6, 29.4, 28.4, 28.2, 25.6, 24.5, 14.0 ppm.

d) (2SR,1'SR,2'SR,3'RS)-2-[(3'-(2"-phenylureidoethyl)-2'-carboxy)cyclopropyl]glycine

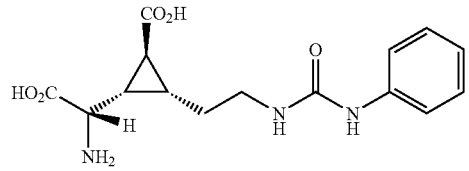

A 2.5M solution of LiOH.H$_2$O (40 eq) in H2O was added to a 0.1M solution of the product of step c) in THF and the mixture was stirred at room temperature overnight. EtOAc was added, the organic layer was separated and the aqueous layer was washed with EtOAc (3×). The aqueous layer was acidified to pH 1 with 1N HCl and extracted in EtOAc (5×). The combined organic layers were dried over MgSO$_4$, filtered and concentrated under vacuum. The residue was dissolved in a 1N solution of HCl in EtOAc and the solution (0.12N) was stirred overnight at room temperature. It was then concentrated under vacuum and the resulting solid was washed with Et$_2$O. The final aminoacid was isolated as a zwitterion by ion exchange chromatography.

(Yield: 42%)

$^{13}$C-NMR (50 MHz, D$_2$O/MeOH-d$_4$): 179.6, 174.0, 159.2, 139.3, 130.2, 125.8, 122.3, 55.4, 40.3, 28.9, 27.8, 27.6, 26.4 ppm

The invention claimed is:

1. A compound of the formula:

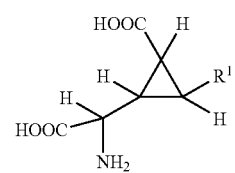

in which:

R$^1$ is (CH$_2$)$_n$Y;

n is 1 or 2;

Y is NHSO$_2$R$^2$ or X$^1$—W—X$^2$—R$^3$;

X$^1$ is O or NH;

W is C=O, C=S, C=NH, or SO$_2$;

X$^2$ is O or NH, provided that X$^1$ and X$^2$ are not both O;

R$^2$ is C$_{1-10}$ alkyl; C$_{2-10}$ alkenyl; C$_{2-10}$ alkynyl; aryl; aryl-C$_{1-10}$ alkyl; aryl-C$_{2-10}$ alkenyl; aryl-C$_{2-10}$ alkynyl; C$_{3-8}$ cycloalkyl or C$_{3-8}$-cycloalkyl-C$_{1-10}$ alkyl; and R$^3$ is hydrogen, C$_{1-10}$ alkyl; C$_{2-10}$ alkenyl; C$_{2-10}$ alkynyl; aryl; aryl-C$_{1-10}$ alkyl; aryl-C$_{2-10}$ alkenyl; aryl-C$_{2-10}$ alkynyl; C$_{3-8}$ cycloalkyl; C$_{3-8}$-cycloalkyl-C$_{1-10}$ alkyl or 1H-tetrazol-5-yl-C$_{1-4}$ alkyl;

or a salt or ester thereof.

2. A compound as claimed in claim 1, which has the configuration

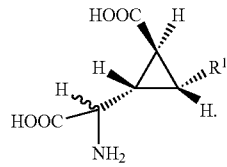

3. A compound as claimed in claim 2, which has the configuration

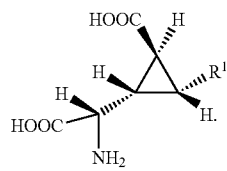

4. A compound according to any one of claims 1 to 3, in which $R^2$ is methyl, ethyl, phenyl or benzyl.

5. A compound according to any one of claims 1 to 3, in which $R^3$ is methyl, phenyl, 2-methoxyphenyl, 3-methoxyphenyl, 4-methoxyphenyl, 2-methylphenyl, 2,6-dimethylphenyl, 3-nitrophenyl, 3-acetylphenyl and 4-trifluoromethylphenyl, or benzyl.

6. A compound as claimed in claim 5, in which $R^1$ is phenylcarbamoyloxymethyl, 2-methoxyphenylcarbamoyloxymethyl, benzylcarbamoyloxymethyl, 3-methoxyphenylcarbamoyloxymethyl, 4-methoxyphenylcarbamoyloxymethyl, 2-methylphenylcarbamoyl-oxymethyl, 2,6-dimethylphenylcarbamoyl-oxymethyl, 3-nitrophenylcarbamoyloxymethyl, 3-acetylphenylcarbamoyl-oxymethyl, 4-trifluoromethylphenylcarbamoyloxymethyl, ethylcarbamoyloxymethyl, cyclohexylcarbamoyloxymethyl, (1-naphthyl)carbamoyloxymethyl, (3-methoxy)phenylcarbamoyl-oxymethyl, phenylureidomethyl, ethylureidomethyl, benzylureidomethyl, benzenesulfonylaminomethyl, phenylthioureidomethyl, phenylcarbamoyloxyethyl, and phenylureidoethyl.

7. A compound as claimed in claim 1, which is selected from:
(2SR,1'SR,2'RS,3'RS)-2-(3'-phenylcarbamoyloxymethyl-2'-carboxycyclopropyl)glycine;
(2SR,1'SR,2'RS,3'RS)-2-(3'-(2-methoxy)phenylcarbamoyl-oxymethyl-2'-carboxycyclopropyl)glycine;
(2SR,1'SR,2'RS,3'RS)-2-(3'-(3-methoxy)phenylcarbamoyl-oxymethyl-2'-carboxycyclopropyl)glycine;
(2SR,1'SR,2'RS,3'RS)-2-(3'-(4-methoxy)phenylcarbamoyl-oxymethyl-2'-carboxycyclopropyl)glycine;
(2SR,1'SR,2'RS,3'RS)-2-(3'-(2-methyl)phenylcarbamoyl-oxymethyl-2'-carboxycyclopropyl)glycine;
(2SR,1'SR,2'RS,3'RS)-2-(3'-(2,6-dimethyl)phenylcarbamoyl-oxymethyl-2'-carboxycyclopropyl)glycine;
(2SR,1'SR,2'RS,3'RS)-2-(3'-(3-nitro)phenylcarbamoyl-oxymethyl-2'-carboxycyclopropyl)glycine;
(2SR,1'SR,2'RS,3'RS)-2-(3'-(3-acetyl)phenylcarbamoyl-oxymethyl-2'-carboxycyclopropyl)glycine;
(2SR,1'SR,2'RS,3'RS)-2-(3'-(4-trifluoromethyl)phenyl-carbamoyloxymethyl-2'-carboxycyclopropyl)glycine;
(2SR,1'SR,2'RS,3'RS)-2-(3'-benzylcarbamoyloxymethyl-2'-carboxycyclopropyl)glycine;
(2SR,1'SR,2'RS,3'RS)-2-(3'-ethylcarbamoyloxymethyl-2'-carboxycyclopropyl)glycine;
(2SR,1'SR,2'RS,3'RS)-2-(3'-cyclohexylcarbamoyloxymethyl-2'-carboxycyclopropyl)-glycine;
(2SR,1'SR,2'RS,3'RS)-2-[3'-(1-naphthyl)carbamoyloxymethyl-2'-carboxycyclopropyl]glycine;
(2SR,1'SR,2'RS,3'RS)-2-[3'-(3-methoxy)phenylcarbamoyl-oxymethyl-2'-carboxycyclopropyl]glycine;
(2SR,1'SR,2'SR,3'RS)-2-(3'-phenylureidomethyl-2'-carboxycyclopropyl)glycine;
(2SR,1'SR,2'SR,3'RS)-2-(3'-benzylureidomethyl-2'-carboxycyclopropyl)glycine;
(2SR,1'SR,2'SR,3'RS)-2-(3'-ethylureidomethyl-2'-carboxycyclopropyl)glycine;
(2SR,1'SR,2'SR,3'RS)-2-(3'-benzenesulfonylaminomethyl-2'-carboxycyclopropyl)glycine;
(2SR,1'SR,2'SR,3'RS)-2-(3'-phenylthioureidomethyl-2'-carboxycyclopropyl)glycine;
(2SR,1'SR,2'SR,3'RS)-2-[(3'-(2"-phenyl-carbamoyloxyethyl)-2'-carboxy)cyclopropyl]-glycine;
and pharmaceutically acceptable salts and esters thereof.

8. A pharmaceutical formulation comprising a compound of formula I as claimed in claims 1, or a pharmaceutically acceptable metabolically labile ester thereof, or a pharmaceutically acceptable salt thereof, together with a pharmaceutically acceptable carrier, diluent or excipient.

9. A process for preparing a compound of formula I as claimed in claims 1, or a salt or ester thereof, which comprises:
(a) deprotecting a compound of formula

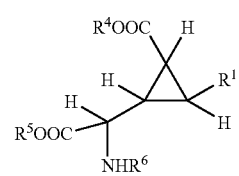

II in which $R^4$ and $R^5$ each independently represents hydrogen or a carboxyl protecting group, $R^6$ represents hydrogen or an amine protecting group, and $R^1$ is as defined in claim 1;

(b) hydrolysing a compound of formula

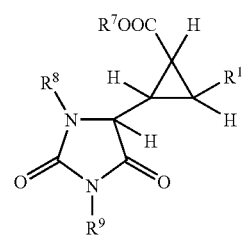

III in which $R^7$ represents a hydrogen atom or a carboxyl protecting group, $R^8$ and $R^9$ each independently represents a hydrogen atom, a $C_{1-4}$ alkyl group, a (2–6C) alkanoyl group, a (3–4C)alkenyl group or a phenyl $C_{1-4}$ alkyl group in which the phenyl group is unsubstituted or substituted by halo, $C_{1-4}$ alkyl, $C_{1-4}$ alkoxy, and $R^1$ is as defined in claim 1; or (c) hydrolysing a compound of formula

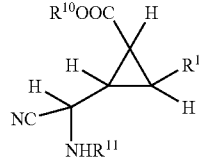
                                                    IV in which $R^{10}$ represents a hydrogen atom or a carboxy protecting group, $R^{11}$ represents a hydrogen atom or an amine protecting group, and $R^1$ is as defined in claim 1; followed when necessary by recovering a diastereomer or isomer of the compound of formula I, or forming a salt or ester thereof.

10. A compound of formula

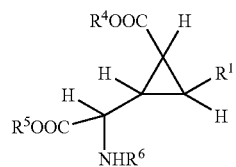
                                                    II in which $R^4$ and $R^5$ each independently represents hydrogen or a carboxyl protecting group, $R^6$ represents hydrogen or an amine protecting group, and $R^1$ is as defined in claim 1.

11. A method of treating a patient suffering from psychosis or anxiety, which comprises administering an effective amount of a compound of formula I according to claim 1, or a pharmaceutically acceptable metabolically labile ester thereof, or a pharmaceutically acceptable salt.

* * * * *